United States Patent [19]
Shturman et al.

[11] Patent Number: 5,897,566
[45] Date of Patent: Apr. 27, 1999

[54] ROTATIONAL ATHERECTOMY DEVICE

[75] Inventors: Leonid Shturman, Minneapolis, Minn.; Andrei Nevzorov, Moscow, Russian Federation

[73] Assignee: Shturman Cardiology Systems, Inc., Minneapolis, Minn.

[21] Appl. No.: 08/679,470

[22] Filed: Jul. 15, 1996

[51] Int. Cl.$^6$ .................................................. A61B 17/22
[52] U.S. Cl. ........................................ 606/159; 606/180
[58] Field of Search .................................. 606/159, 180; 604/22

[56] References Cited

U.S. PATENT DOCUMENTS

| | | | |
|---|---|---|---|
| 4,990,134 | 2/1991 | Auth | 604/22 |
| 5,158,564 | 10/1992 | Schnepp-Pesch et al. | 606/159 |
| 5,192,291 | 3/1993 | Pannek | 606/159 |
| 5,314,438 | 5/1994 | Shturman | 606/159 |
| 5,358,485 | 10/1994 | Vance et al. | 606/159 X |
| 5,395,311 | 3/1995 | Andrews | 606/159 X |
| 5,490,859 | 2/1996 | Mische et al. | 606/159 |

FOREIGN PATENT DOCUMENTS 2055991  3/1996  Russian Federation .

*Primary Examiner*—Michael H. Thaler
*Attorney, Agent, or Firm*—Gregory P. Kaihoi

[57] ABSTRACT

An atherectomy device for removing tissue from an artery. The device includes a flexible, elongated drive shaft rotatable about a guide wire, the drive shaft having an enlarged diameter tissue removal section. The drive shaft and the enlarged diameter tissue removal section are comprised of helically wound wire. Wire turns of the proximal portion of the tissue removal section have diameters that gradually increase distally at a generally constant rate thereby forming generally the shape of a cone. Wire turns of the distal portion of the enlarged diameter tissue removal section have diameters that gradually decrease distally thereby forming a generally convex distal portion. At least part of the tissue removal section includes an external coating of an abrasive material to define an abrasive segment of the drive shaft. The drive shaft may include a reduced diameter segment located near the enlarged diameter tissue removal section to facilitate smooth rotation of the drive shaft and its tissue removal section about the guide wire when the atherectomy device is rotated at high speeds. Preferably such a reduced diameter segment is provided just proximal to the enlarged diameter tissue removal section, and preferably the entire portion of the drive shaft distal to the enlarged diameter tissue removal section also has a similarly reduced diameter. The maximum outer diameter and length of the abrasive segment may be selected so that, at operational rotational speeds and under load, at least some of the wire turns of the proximal portion of the enlarged diameter tissue removal section unwind from their at-rest diameter to an effective outer diameter which is the same as or larger than the maximum outer diameter of the abrasive segment.

47 Claims, 37 Drawing Sheets

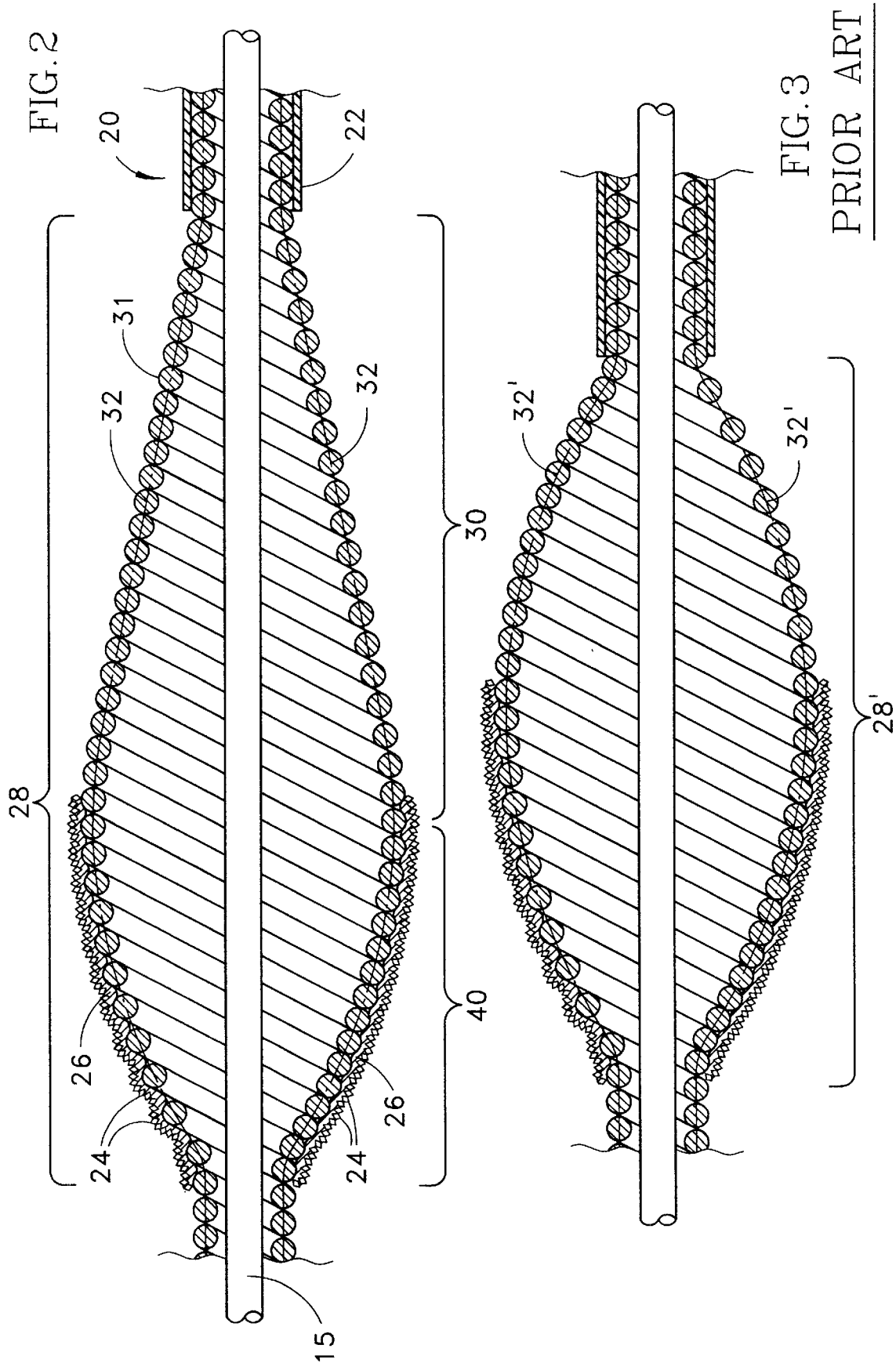

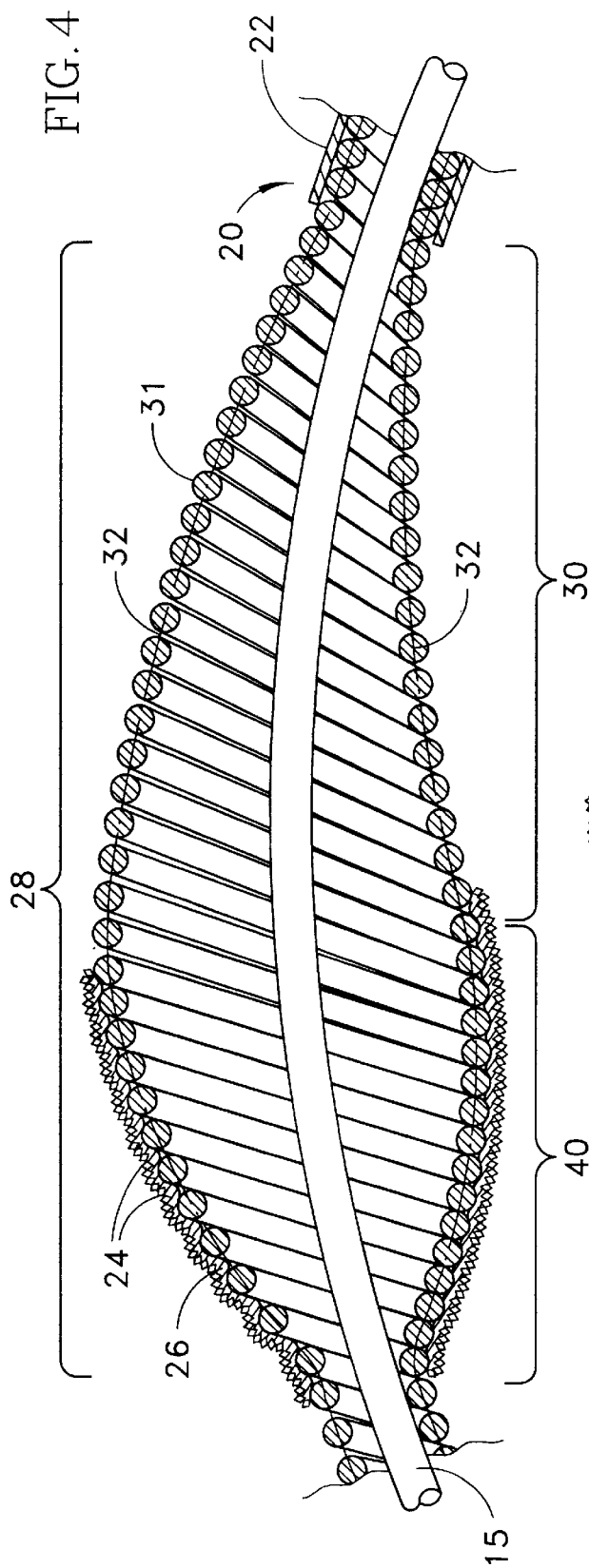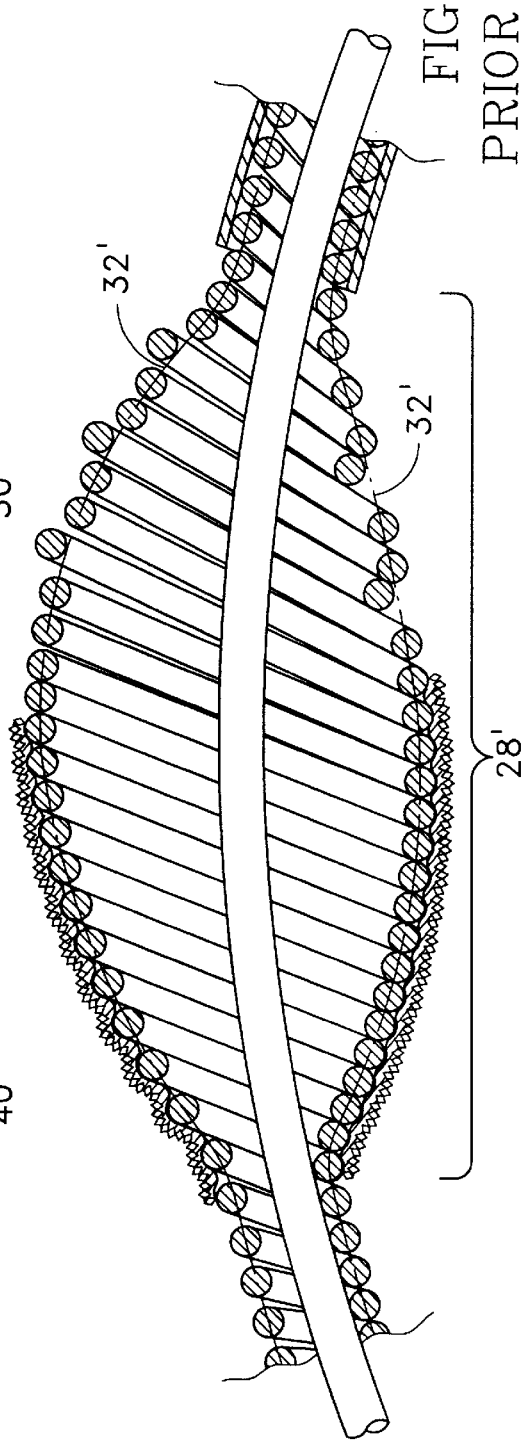
FIG. 4
FIG. 5 PRIOR ART

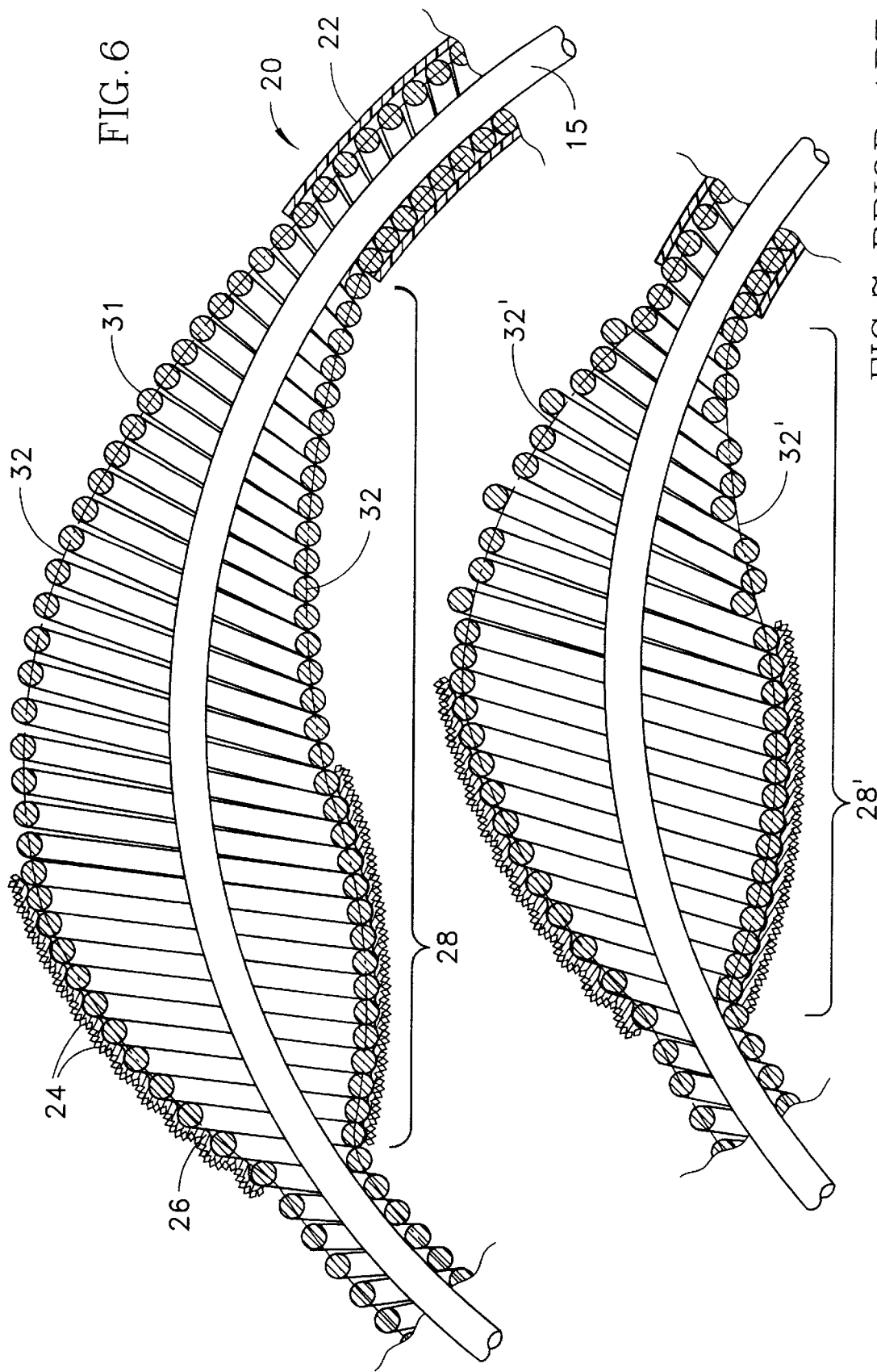

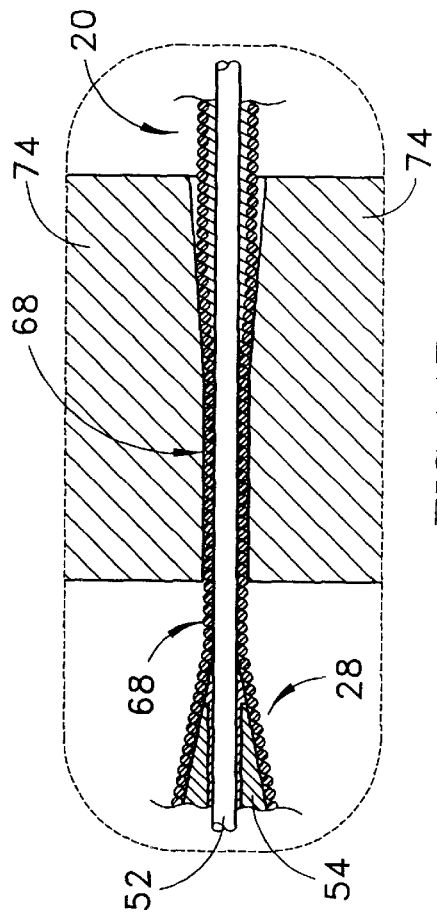
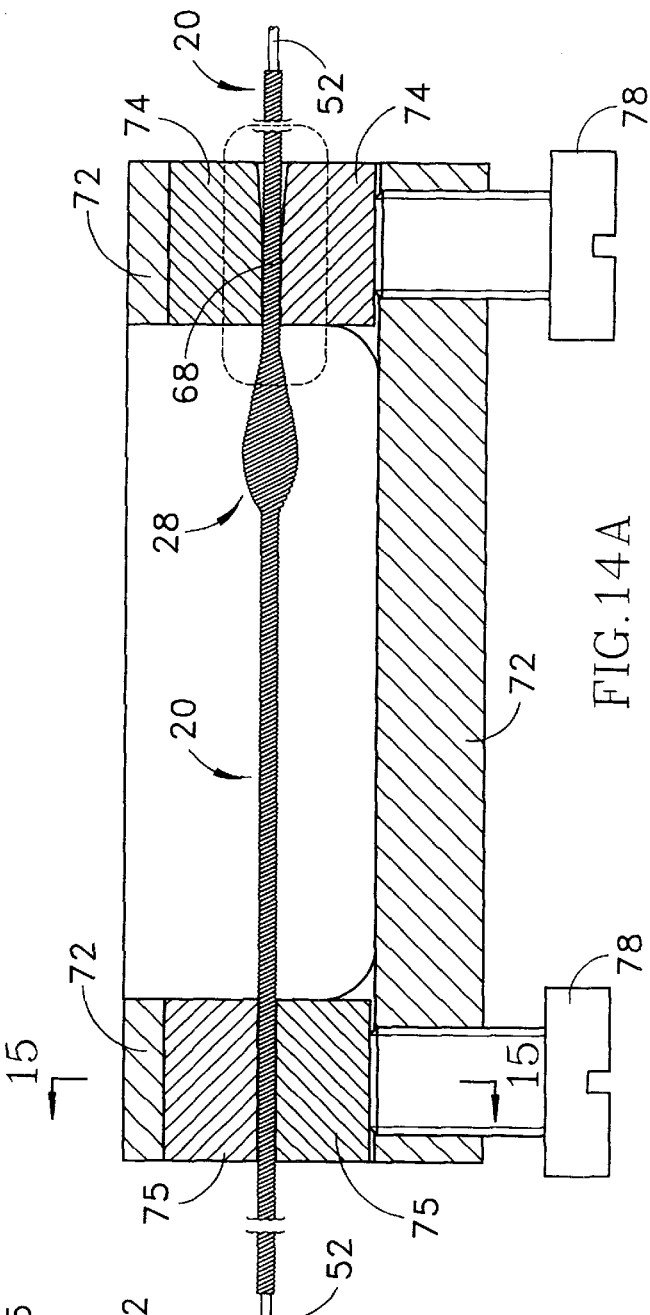
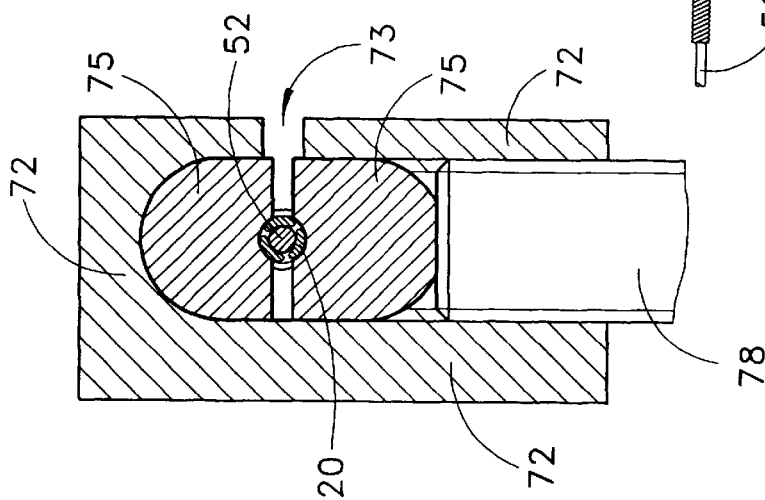
FIG. 14B
FIG. 14A
FIG. 15

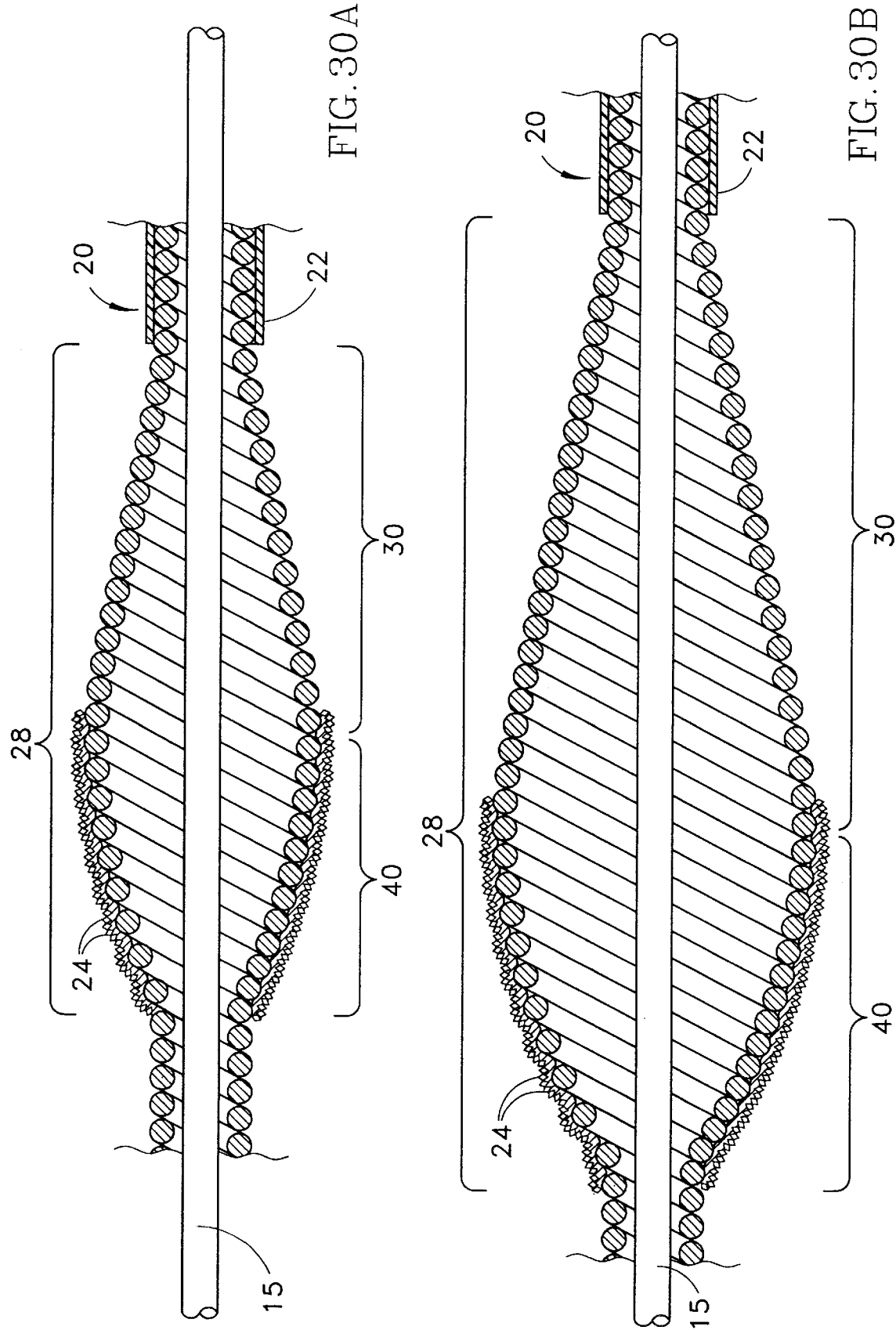

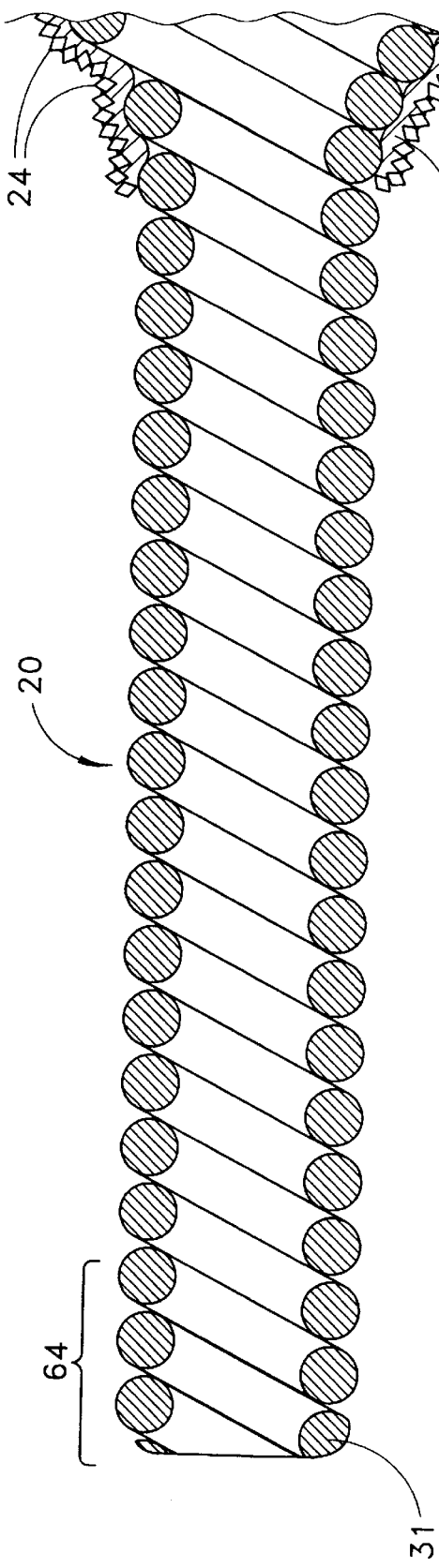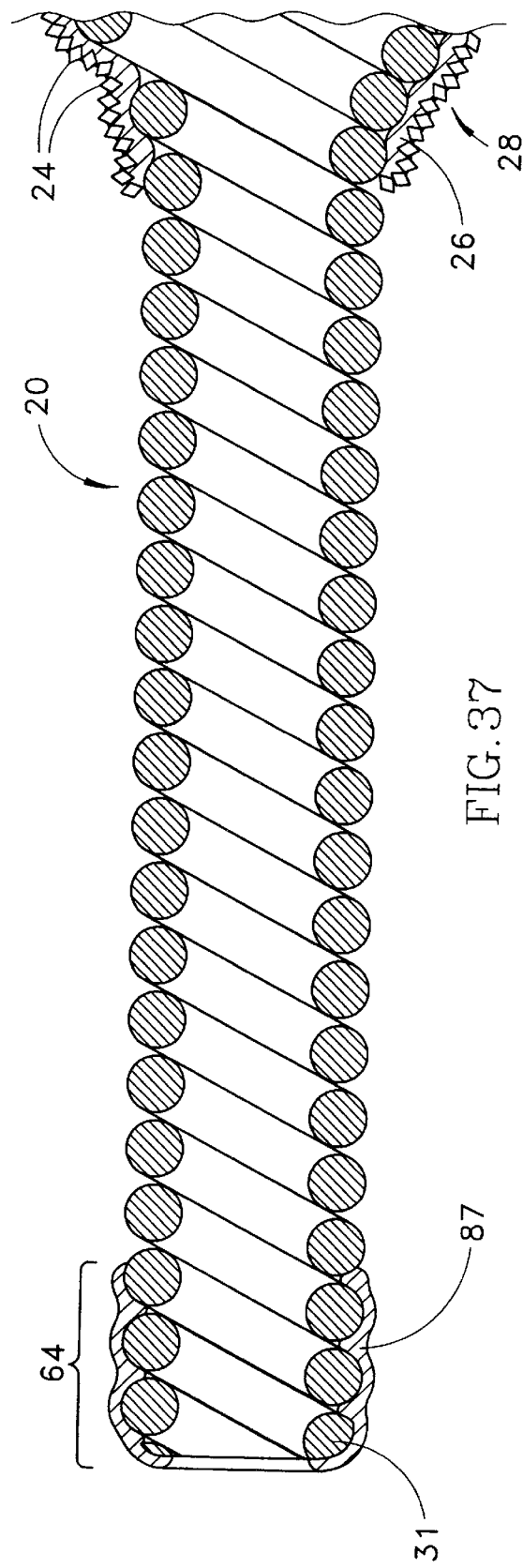

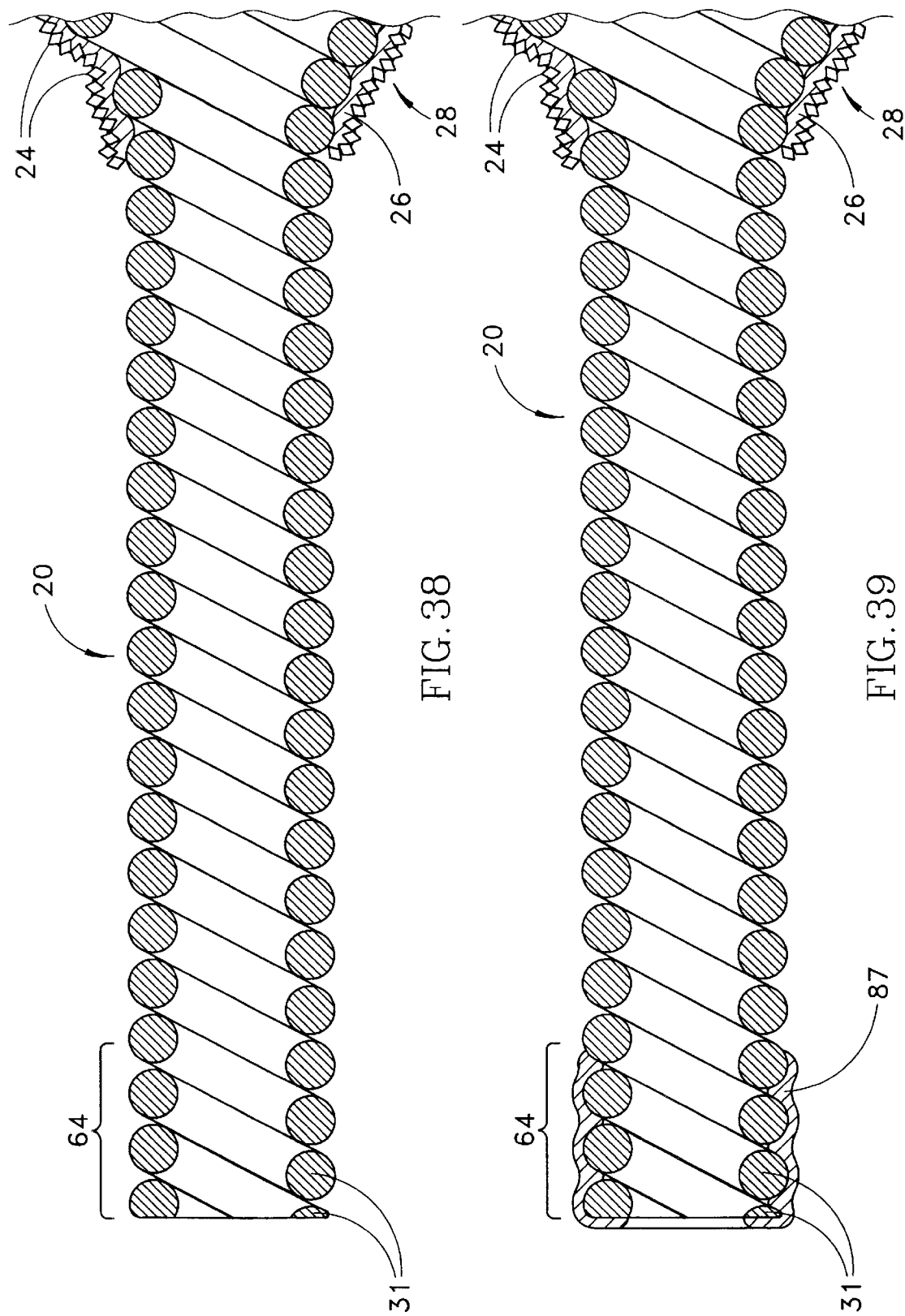

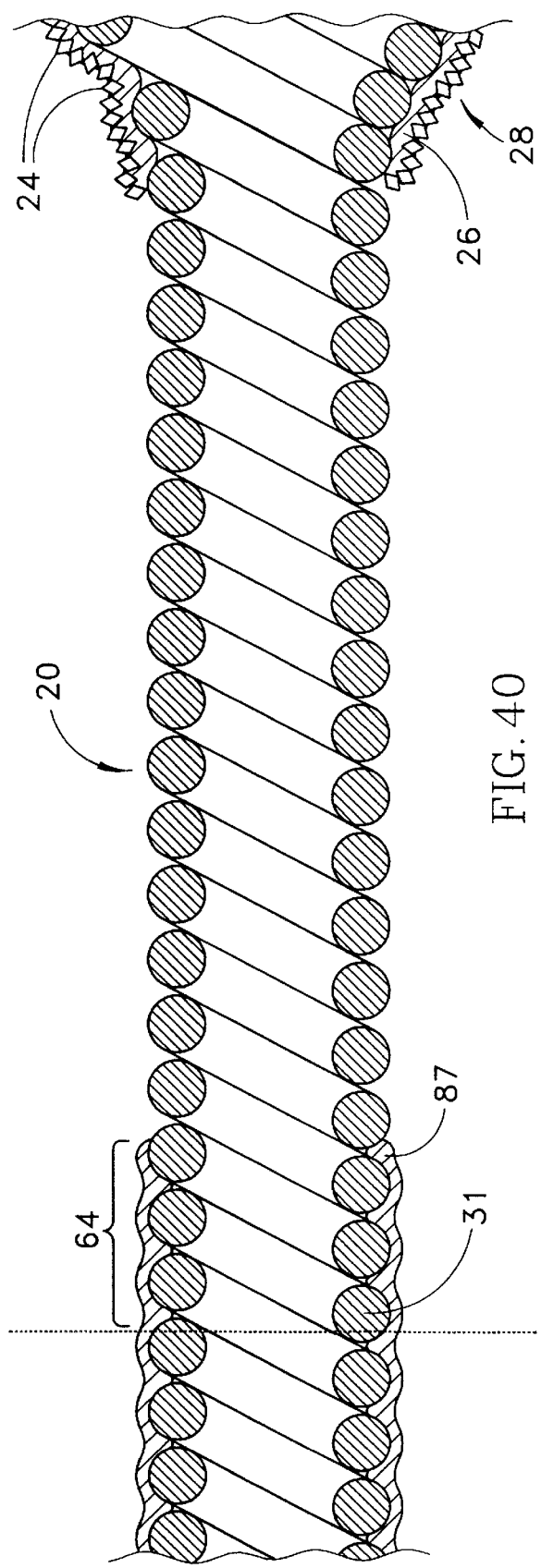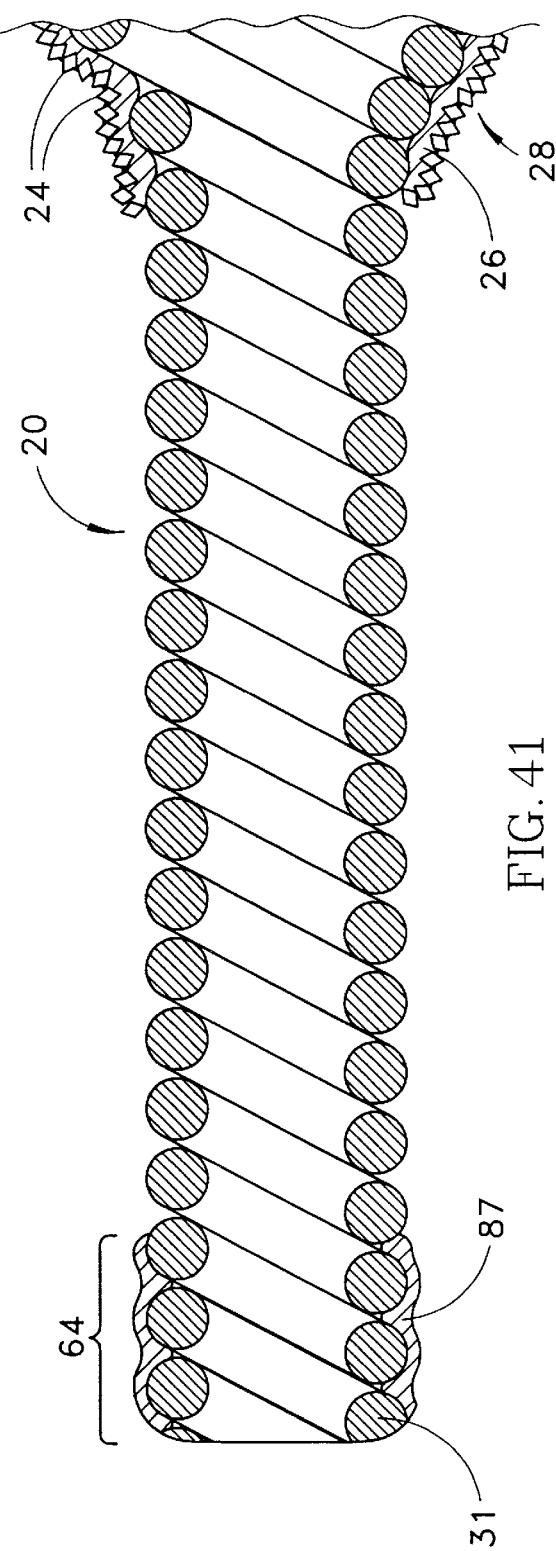

ROTATIONAL ATHERECTOMY DEVICE

TECHNICAL FIELD

The invention relates to devices and methods for removing tissue from body passageways, such as removal of atherosclerotic plaque from arteries, utilizing a rotational atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material such as diamond grit (diamond particles or dust) is carried at the distal end of a flexible drive shaft. The rotating burr is rigid and inflexible, however, making navigation around tight bends or curves in an artery more difficult, and making the removal of stenotic lesions in such bends or curves equally difficult.

U.S. Pat. No. 5,314,438 (Shturman) shows another atherectomy device having a drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery. In some of the embodiments depicted in the Shturman patent, wire turns of the enlarged diameter segment of the drive shaft are supported by a bushing. Even though this bushing may be made of a flexible material, nevertheless it decreases somewhat the flexibility of the enlarged diameter abrasive segment of the drive shaft.

Unless a bushing within the enlarged diameter section is utilized, Applicants have found that adjacent wire strands of this section can fall out of alignment with one another when the enlarged diameter portion of the drive shaft is bent around a curve of a relatively small radius.

SUMMARY OF THE INVENTION

The invention provides an atherectomy device comprised of a flexible, elongated drive shaft having an enlarged diameter tissue removal section which retains substantial flexibility while reducing the tendency of the wire turns to fall out of alignment with one another. The tissue removal section of the drive shaft of this atherectomy device includes proximal and distal portions comprised of helically wound wire, wire turns of the proximal portion of the tissue removal section having diameters that progressively increase distally at a generally constant rate thereby forming generally the shape of a cone. Wire turns of the distal portion of the enlarged diameter tissue removal section have diameters that gradually decrease distally thereby forming a generally convex distal portion.

The conical shape of the proximal portion of the tissue removal section substantially reduces the tendency of the wire turns to fall out of alignment with one another, without the need to utilize a bushing, thereby preserving substantial flexibility in the enlarged diameter section.

At least part of the tissue removal section includes an external coating of an abrasive material, secured to the wire turns of the drive shaft by a suitable binder, to define an abrasive segment of the drive shaft. Preferably the binder also secures some of the adjacent wire turns of the tissue removal section to one another, most preferably throughout a distal portion of the tissue removal section.

In a preferred embodiment, the drive shaft of the atherectomy device includes a reduced diameter segment, such segment being located near the tissue removal section of the drive shaft to function as a bearing for rotation of the drive shaft about a guide wire. The reduced clearance between the guide wire and the inner surface of the reduced diameter segment is less than in other portions of the drive shaft and is intended to reduce vibrations of the tissue removal section and facilitate smooth rotation of the drive shaft and its tissue removal section about the guide wire when the atherectomy device is rotated at high speeds. Two or more of such reduced diameter segments may be included, preferably at least one being located distally of the tissue removal section of the drive shaft, and at least one being located proximally of the tissue removal section of the drive shaft. Preferably such reduced diameter segments are located within about one inch from the enlarged diameter tissue removal section, and most preferably within about a quarter inch from such tissue removal section.

The maximum outer diameter and length of the abrasive segment of the enlarged diameter tissue removal section may be selected so that, at operational rotational speeds and under load, at least some of the wire turns of the proximal portion of the enlarged diameter tissue removal section unwind from their at-rest diameter to an effective outer diameter which is the same as or larger than the maximum outer diameter of the abrasive segment.

The drive shaft of the atherectomy device may include a distal end segment having an outer diameter which decreases distally to define a generally convex outer surface. At least a portion of this distal end segment may be provided with an external coating of an abrasive material to define a second abrasive segment at the very distal end of the drive shaft. Such an abrasive coated distal end segment facilitates passage of the rotating drive shaft of the atherectomy device across even very tight stenoses.

BRIEF DESCRIPTION OF THE DRAWINGS

FIG. 2 is a broken-away, longitudinal cross-sectional view of the enlarged diameter tissue removal section of the atherectomy device shown in FIG. 1;

FIG. 3 is a broken-away, longitudinal cross-sectional view of the enlarged diameter tissue removal section of a prior art atherectomy device;

FIG. 4 is a broken-away, longitudinal cross-sectional view of the atherectomy device of FIG. 2 depicted in a slightly curved configuration;

FIG. 5 is a broken-away, longitudinal cross-sectional view of the prior art atherectomy device of FIG. 3 depicted in a slightly curved configuration;

FIG. 6 is a broken-away, longitudinal cross-sectional view of the atherectomy device of FIG. 2 depicted in a more tightly curved configuration;

FIG. 7 is a broken-away, longitudinal cross-sectional view of the prior art atherectomy device of FIG. 3 depicted in a more tightly curved configuration;

FIG. 9A is an enlarged view of the distal section of the atherectomy device of FIG. 9;

FIG. 10A is an enlarged view of the distal section of the atherectomy device of FIG. 10;

FIG. 11A is an enlarged view of the distal section of the atherectomy device of FIG. 11;

FIG. 12A is an enlarged view of the distal section of the atherectomy device of FIG. 12;

FIG. 12B is an enlarged view of portions of the proximal section of the atherectomy device of FIG. 12;

FIG. 13A is an enlarged view of the distal section of the atherectomy device of FIG. 13;

FIG. 13B is an enlarged view of portions of the proximal section of the atherectomy device of FIG. 13;

FIG. 14A is a longitudinal cross-sectional view of the clamp of FIG. 14;

FIG. 14B is an enlarged view showing in longitudinal cross-section details of a portion of FIG. 14A;

FIG. 15 is an enlarged cross-sectional view, partially broken away, of FIG. 14A, taken along lines 15—15 thereof;

FIG. 16A is an enlarged view of the distal section of the atherectomy device of FIG. 16;

FIG. 16B is an enlarged view of portions of the proximal section of the atherectomy device of FIG. 16;

FIG. 17A is an enlarged view of the distal section of the atherectomy device of FIG. 17;

FIG. 17B is an enlarged view of portions of the proximal section of the atherectomy device of FIG. 17;

FIGS. 30A and 30B are broken-away, longitudinal cross-sectional views of atherectomy devices of the invention, illustrating proportionality of such devices of different sizes;

FIG. 36 is a broken-away, longitudinal cross-sectional view of the distal section of a modified atherectomy device of the invention with the distal end rounded off;

FIG. 37 is a broken-away, longitudinal cross-sectional view of the embodiment of FIG. 36 with the distal end coated with a bonding material to secure the wire turns to one another;

FIG. 38 is a broken-away, longitudinal cross-sectional view of the distal section of a modified atherectomy device of the invention with the distal end trimmed off "square";

FIG. 39 is a broken-away, longitudinal cross-sectional view of the embodiment of FIG. 38 with the distal end coated with a bonding material to secure the wire turns to one another;

FIG. 40 is a broken-away, longitudinal cross-sectional view of the distal section of a modified atherectomy device of the invention with the distal end electroplated before being trimmed to its finished length;

FIG. 41 is a broken-away, longitudinal cross-sectional view of the embodiment of FIG. 40 with the distal end trimmed to its finished length;

DETAILED DESCRIPTION OF THE INVENTION

Figure 1:
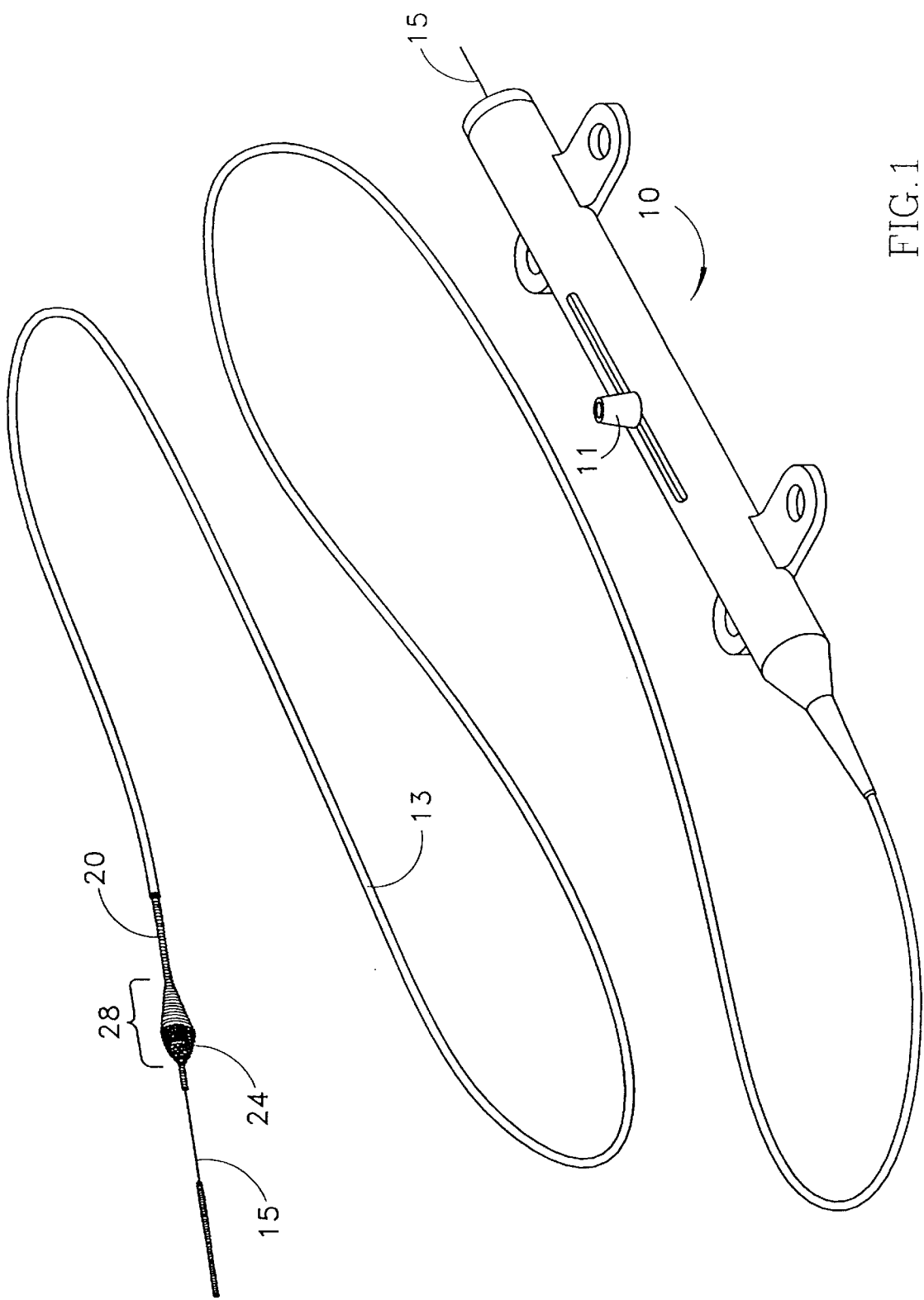
FIG. 1 is a perspective view of an atherectomy device of the invention.

FIG. 1 illustrates a typical rotational atherectomy device of the invention. The device includes a handle portion 10, an elongated, flexible drive shaft 20 having an enlarged diameter tissue removal section 28, and an elongated catheter 13 extending distally from the handle portion 10. The drive shaft 20 is constructed from helically coiled wire, preferably multifilar. The catheter 13 has a lumen in which most of the length of the drive shaft 20 is disposed, the enlarged diameter tissue removal section 28 extending distally beyond the distal end of the catheter 13. The drive shaft 20 also contains an inner lumen, permitting the drive shaft 20 to be advanced and rotated over a guide wire 15.

The handle 10 desirably contains a turbine (or similar rotational drive mechanism) for rotating the drive shaft 20 at high speeds. The handle 10 typically may be connected to a power source (such as compressed air), a source of physiologic solution (used for cooling and lubrication), through suitable tubing, which are not illustrated for the sake of clarity (details regarding such handles and associated instrumentation are well know in the industry, and are described, e.g., in U.S. Pat. No. 5,314,407, issued to Auth). The handle 10 also desirably includes a control knob 11 for advancing and retracting the turbine and drive shaft 20 with respect to the catheter 13 and the body of the handle.

FIG. 2 shows more details of the enlarged diameter tissue removal section 28. The section 28 includes proximal and distal portions. Wire turns 31 of the proximal portion 30 of the tissue removal section 28 have diameters that progressively increase distally at a generally constant rate, thereby forming generally the shape of a cone. The conical shape of the proximal portion 30 of the tissue removal section 28 gives desirable performance characteristics, which will be discussed in greater detail below. Wire turns of the distal portion 40 have diameters that gradually decrease distally (preferably at a varying rate) thereby forming a generally convex distal portion 40.

At least part of the tissue removal section 28 (preferably the distal portion 40 of the tissue removal section 28) includes an external coating of an abrasive material 24 to define an abrasive segment of the drive shaft 20. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the wire turns of the drive shaft 20 by a suitable binder 26—such attachment may be achieved using well known techniques, such as conventional electroplating or fusion technologies (see, e.g., U.S. Pat. No. 4,018,576).

Preferably a portion of the drive shaft 20 proximal to the enlarged tissue removal section 28 is encased in a thin, flexible, low friction sheath or coating 22. In a preferred embodiment, the sheath or coating 22 is sufficiently long so that its proximal end remains disposed inside the catheter 13 even when the drive shaft 20, with its enlarged diameter tissue removal section 28 is fully advanced distally with respect to the catheter 13. Applicants have successfully utilized heat shrinkable polytetrafluoroethylene tubing to make such sheath 22. Such sheath or coating 22 may be made from other suitable materials.

FIG. 3 depicts an enlarged diameter tissue removal section 28' of a prior art atherectomy device similar to that described in U.S. Pat. No. 5,314,438 (Shturman). In both FIGS. 2 and 3, the enlarged diameter tissue removal sections 28 and 28' are shown in a generally straight (i.e., "at rest") configuration.

FIGS. 4 and 5 illustrate the differences in certain performance characteristics of the atherectomy device of the invention in comparison to the prior art device. In these figures, each of the devices has been bent into a curved configuration with a radius of curvature which is relatively large. Each of the devices is illustrated as being constructed from tri-fiar helical windings of wire, and all but the abrasive segments of both devices are generally flexible.

Notice that in FIG. 5 (the prior art version), adjacent windings in the proximal portion of the enlarged diameter section 28' have slipped past one another, coming out of smooth alignment. This phenomena is not seen in the distal portion of the enlarged diameter section 28' because the binder used to secure the abrasive particles to the turns of the drive shaft also serves to secure adjacent wire turns to one another, thus keeping such wire turns in relative alignment with one another.

FIG. 4 illustrates an advantage of the invention over the prior art. Applicants have found that by providing the proximal portion 30 of the enlarged diameter section 28 of the drive shaft 20 with a generally conical shape, the wire turns 31 tend to stay in alignment as this portion of the drive shaft is bent into a curved configuration. Alignment of the wire turns 31 in FIG. 4 can easily be compared to the misalignment of the wire turns in FIG. 5 by reference to the hypothetical center lines 32 and 32'. The atherectomy device of FIG. 4 illustrates a device having an enlarged diameter tissue removal section 28 with a maximum diameter of about 2.1 mm, bent into a curved configuration with a radius of curvature of about 10 mm.

FIGS. 6 and 7 illustrate this effect even more dramatically, as both an atherectomy device of the invention (FIG. 6) and a prior art atherectomy device (FIG. 7) are bent into a curved configuration with a smaller radius of curvature. The misalignment of wire turns in the prior art device (FIG. 7) becomes more severe, while the wire turns of the device of the invention (FIG. 6) stay well-aligned. The atherectomy device of FIG. 6 illustrates a device having an enlarged diameter tissue removal section 28 with a maximum diameter of about 2.1 mm, bent into a curved configuration with a radius of curvature of about 5 mm.

Figure 8:
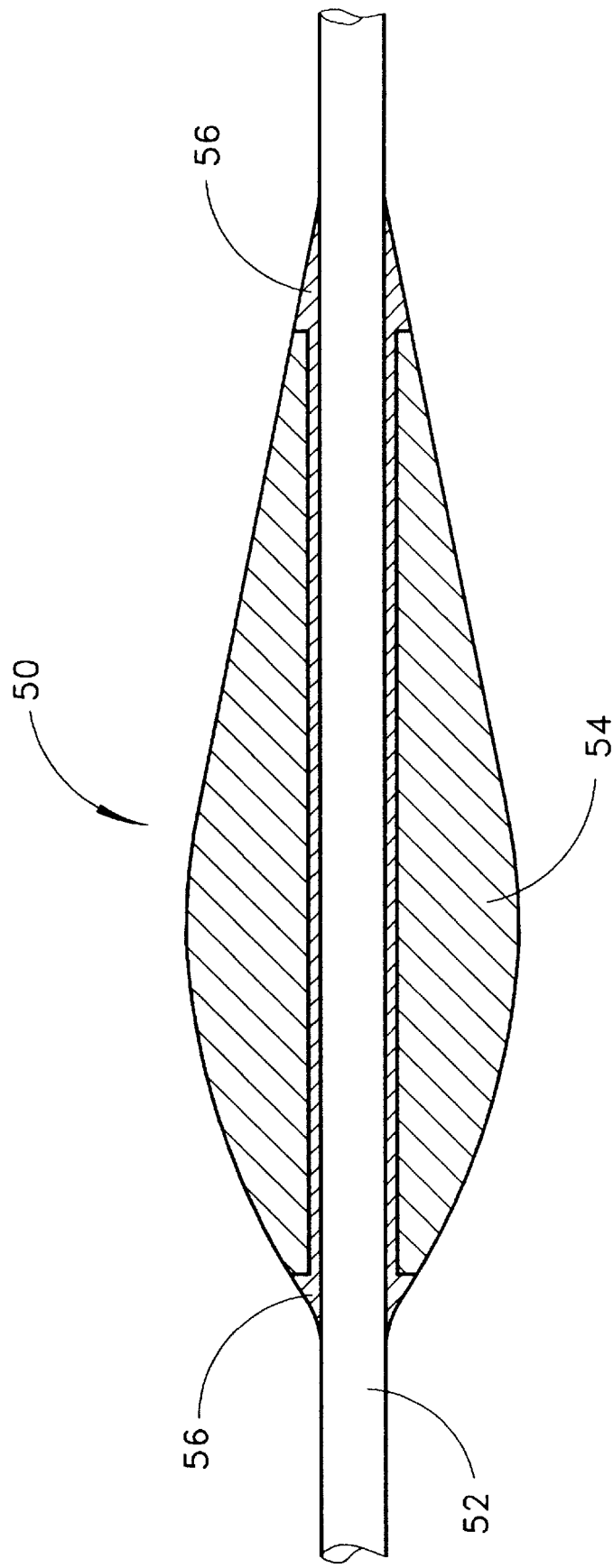
FIG. 8 is a broken-away, longitudinal cross-sectional view of a mandrel used in manufacturing a rotational atherectomy device of the invention.

Helically wound multifilar drive shafts usable in the invention may be manufactured by winding suitable wires about a mandrel. FIG. 8 depicts a mandrel 50 usable to construct the enlarged diameter tissue removal section 28 of the atherectomy device depicted in FIGS. 2, 4 and 6. The mandrel includes a round central mandrel shaft 52 having a generally constant diameter along its entire length. An enlarged portion 54, may be manufactured from suitable materials. For example, it may be machined from, e.g., brass (such as round brass rod sold by Vincent Metals, of Minneapolis, Minn. as "low leaded" brass rod comprised of 62.0% copper, 36.2% zinc and 1.8% lead, or "high speed— free cutting" brass rod comprised of 61.5% copper, 35.5% zinc and 3.0% lead). This enlarged portion 54 is disposed on the mandrel shaft 52 at the desired location, and is then secured in place with a suitable material, such as solder 56. Preferably the solder composition is 61% tin and 39% lead. Also, the flux used in soldering the enlarged portion 54 to the mandrel shaft 52 preferably is comprised of 75% $ZnCl_2$ and 25% $NH_4Cl$, these compounds being dissolved in distilled water at maximum concentration (i.e., creating a saturated solution). The solder joint may be further machined or sanded to achieve a desirably smooth transition from the diameter of the enlarged portion 54 to the diameter of the mandrel shaft 52.

After the mandrel 50 is so constructed, suitable wires may be wound about the mandrel shaft 52 and the enlarged portion 54, and the entire unit (or, preferably, just the enlarged diameter tissue removal section 28, together with that portion of the drive shaft 20 that is distal to the enlarged diameter tissue removal section 28 and about 80 mm of the drive shaft proximal to the enlarged diameter tissue removal section 28) may then be heat treated to give the wire the desired "set." Preferably the heat treatment is in the range of about 360° C. to about 560° C. for about one hour to give the wire the desired set. The particular temperature selected will depend on the type of wire used and the maximum diameter of the enlarged diameter tissue removal section. Applicants have successfully used stainless steel helically wound wire with a diameter of about 0.006 inches for drive shafts having tissue removal sections with diameters of about 1.75 mm or less, and about 0.007 inches for drive shafts having tissue removal sections with diameters of about 1.75 mm or more. Applicants have successfully used stainless steel wire available from Fort Wayne Metals Research Products Corp. (Fort Wayne, Ind.) under the names "Spring Temper" and "Hyten" (both being type 304 stainless steel wire).

After the heat treatment has been completed, the mandrel is then removed. Because the enlarged portion 54 of the mandrel has a diameter exceeding the diameter of the mandrel shaft 52, the enlarged portion 54 of the mandrel 50 must be removed before the remaining portion of the mandrel may be withdrawn from within the helically wound drive shaft. Applicants have found that the enlarged portion 54 of the mandrel may suitably be removed by constructing the mandrel from materials different from the drive shaft wire, and then dissolving at least the enlarged portion 54 of the mandrel 50. For example, the mandrel shaft 52 may be made from high carbon steel, the enlarged portion 54 from brass (as described above), and the helically wound wire from stainless steel (such as the type 304 Spring Temper or Hyten stainless steel wire mentioned above). The enlarged portion 54 of the mandrel (together with the enlarged diameter tissue removal section 28 as well as that portion of the drive shaft 20 that is distal to the enlarged diameter tissue removal section and about 50 mm of the drive shaft proximal to the enlarged diameter tissue removal section 28) is then immersed in boiling nitric acid (typically at about 107° C.) $\rho$=1.33 $g/cm^3$ for, e.g., about 15–45 minutes until the entire immersed section of the mandrel (including both the enlarged portion 54 of the mandrel and the immersed section of the mandrel shaft 52) is completely dissolved. The actual time it takes to completely dissolve the immersed portion of the mandrel 50 depends on the size of the spaces between wire turns of the drive shaft and diameter of the enlarged portion 54 of the mandrel (smaller spaces require longer times, and larger diameters of the enlarged portion 54 of the mandrel require longer times). The drive shaft wires are not adversely affected by the nitric acid. The remaining proximal portion of the mandrel shaft 52 may then be easily removed. After the mandrel shaft 52 is removed, then the entire drive shaft preferably is heat treated at temperatures ranging from 200 to 300° C. to relieve stresses in the wire turns of the drive shaft. The drive shaft then is finished by electropolishing.

Figure 9:
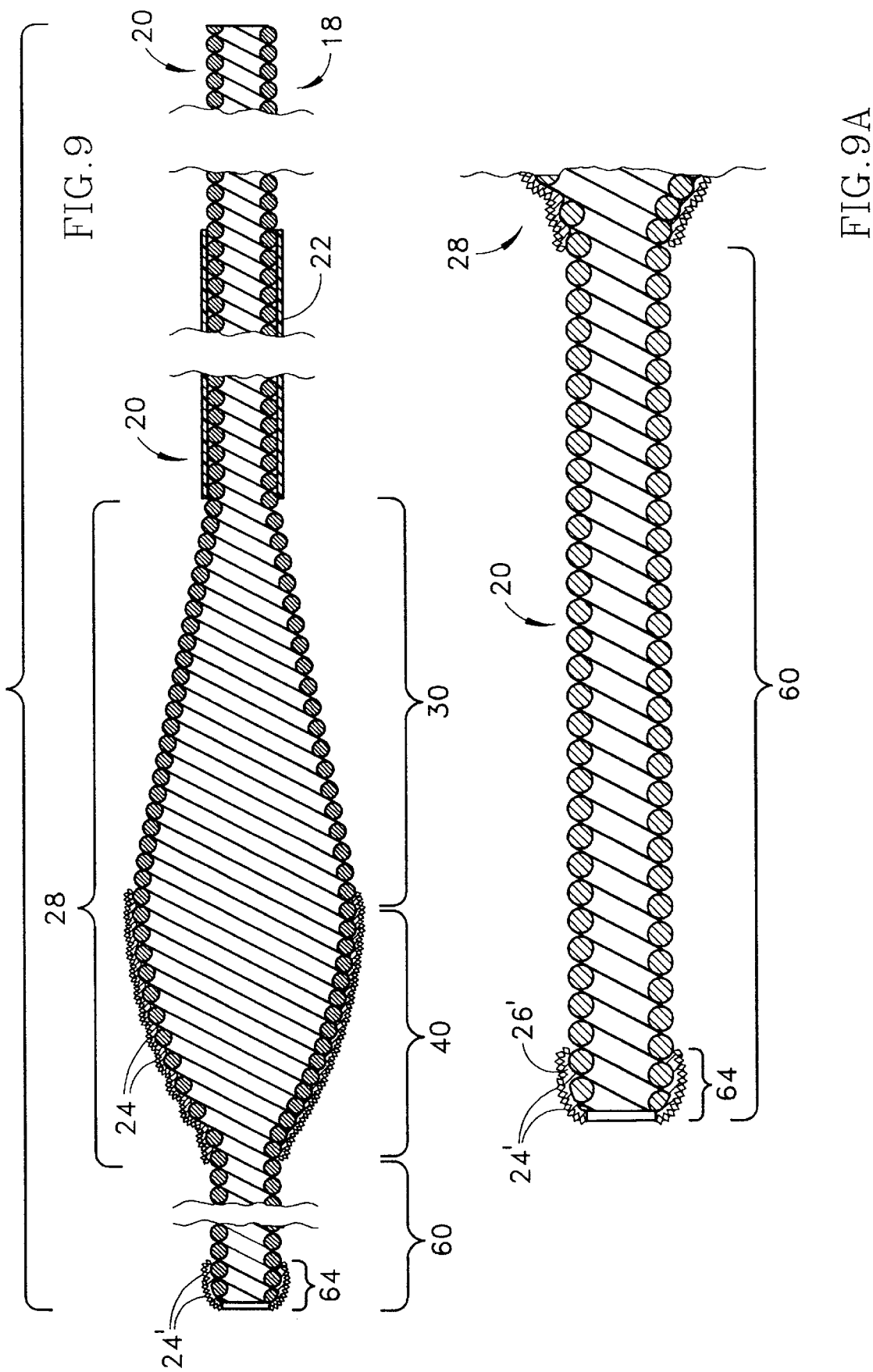
FIG. 9 is a broken-away, longitudinal cross-sectional view of a modified embodiment of the invention having a distal end segment coated with abrasive material to define a second abrasive segment at the very distal end of the atherectomy device.

FIGS. 9 and 9A depict the entire length of a modified embodiment of the atherectomy device of the invention (including the proximal end portion 18 of the drive shaft 20) in which the distal section 60 of the drive shaft 20 (i.e., that portion of the drive shaft 20 which is distal to the enlarged diameter tissue removal section 28 of the drive shaft 20) includes a distal end segment 64. Desirably at least a portion of the distal end segment 64 is provided with an external coating of an abrasive material 24' (secured by a suitable binder 26') to define a second abrasive segment at the distal end of the drive shaft 20. This second abrasive segment preferably has an outer diameter which decreases distally to define a generally convex outer surface—preferably the inner diameter of the distal end segment is generally constant, and, thus, it is the cross-sectional thickness of the wire turns of the distal end segment 64 which decreases distally to form the generally convex outer surface of the distal end segment 64 of the drive shaft 20.

The second abrasive segment of the drive shaft 20 enables the rotating drive shaft of the atherectomy device to be advanced across even a very tight stenosis. In use, the rotating abrasive segment of the distal end segment 64 opens the stenosis to a diameter sufficient to permit advancement of the distal section 60 of the drive shaft 20 across the stenosis until the abrasive material 24 of the enlarged diameter section 28 of the drive shaft 20 engages the stenotic material. The enlarged diameter section 28 then is used to open the stenosis to a diameter equal to (or, due to slight vibrations of the enlarged diameter section 28, usually somewhat larger than) the largest outer diameter of the enlarged diameter section 28 of the drive shaft 20.

Figure 10:
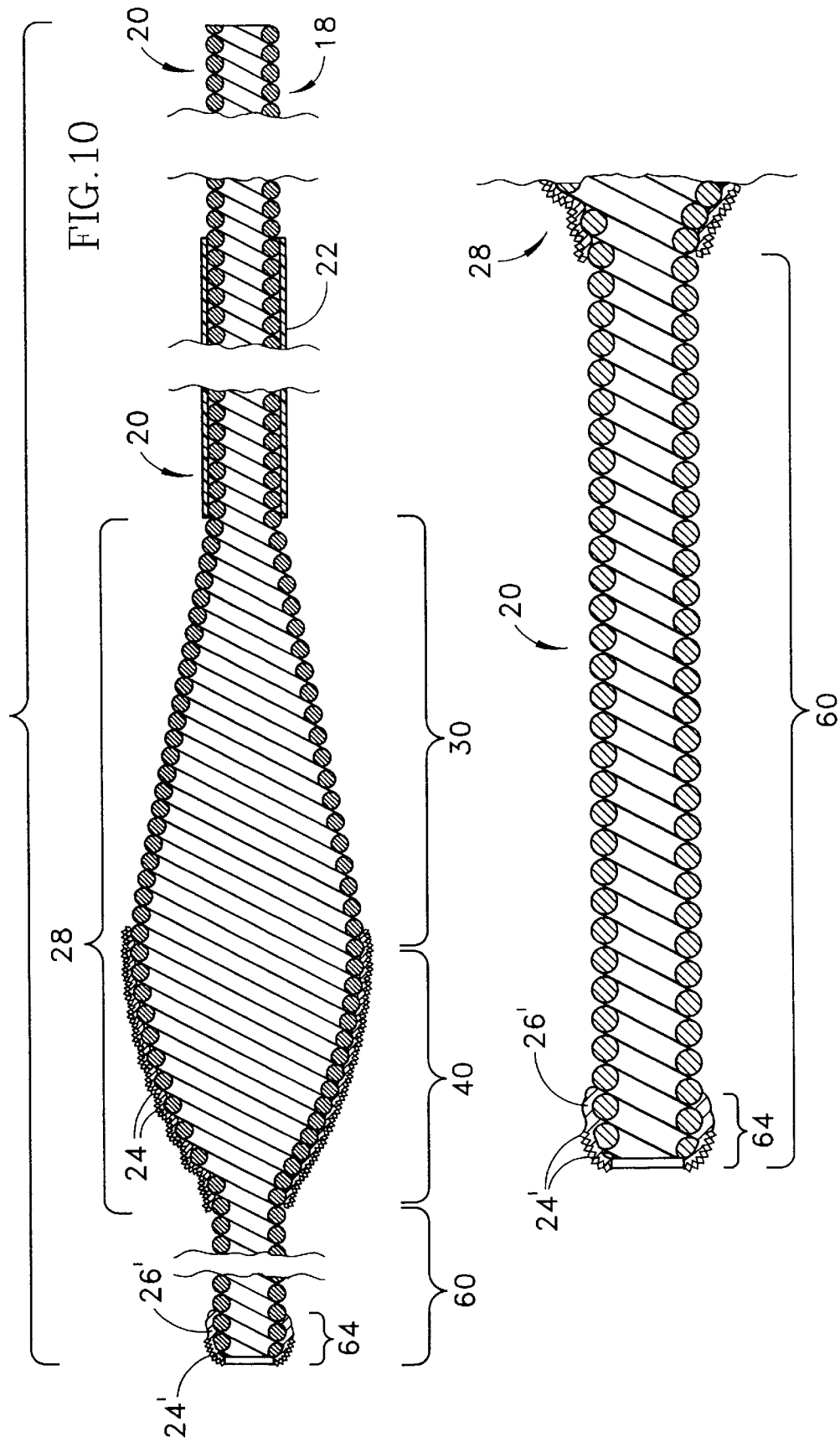
FIG. 10 is a broken-away, longitudinal cross-sectional view of a modified embodiment of the invention having a distal end segment partially coated with abrasive material to define a second abrasive segment at the very distal end of the atherectomy device.

FIG. 9A shows abrasive material 24' covering essentially all of the distal end segment 64. FIGS. 10 and 10A depict a slightly modified embodiment where the binder material 26' secures adjacent wire turns of the distal end segment to one another (as in FIGS. 9 and 9A), but abrasive material 24' covers only a portion of the binder material 26'.

Figure 11:
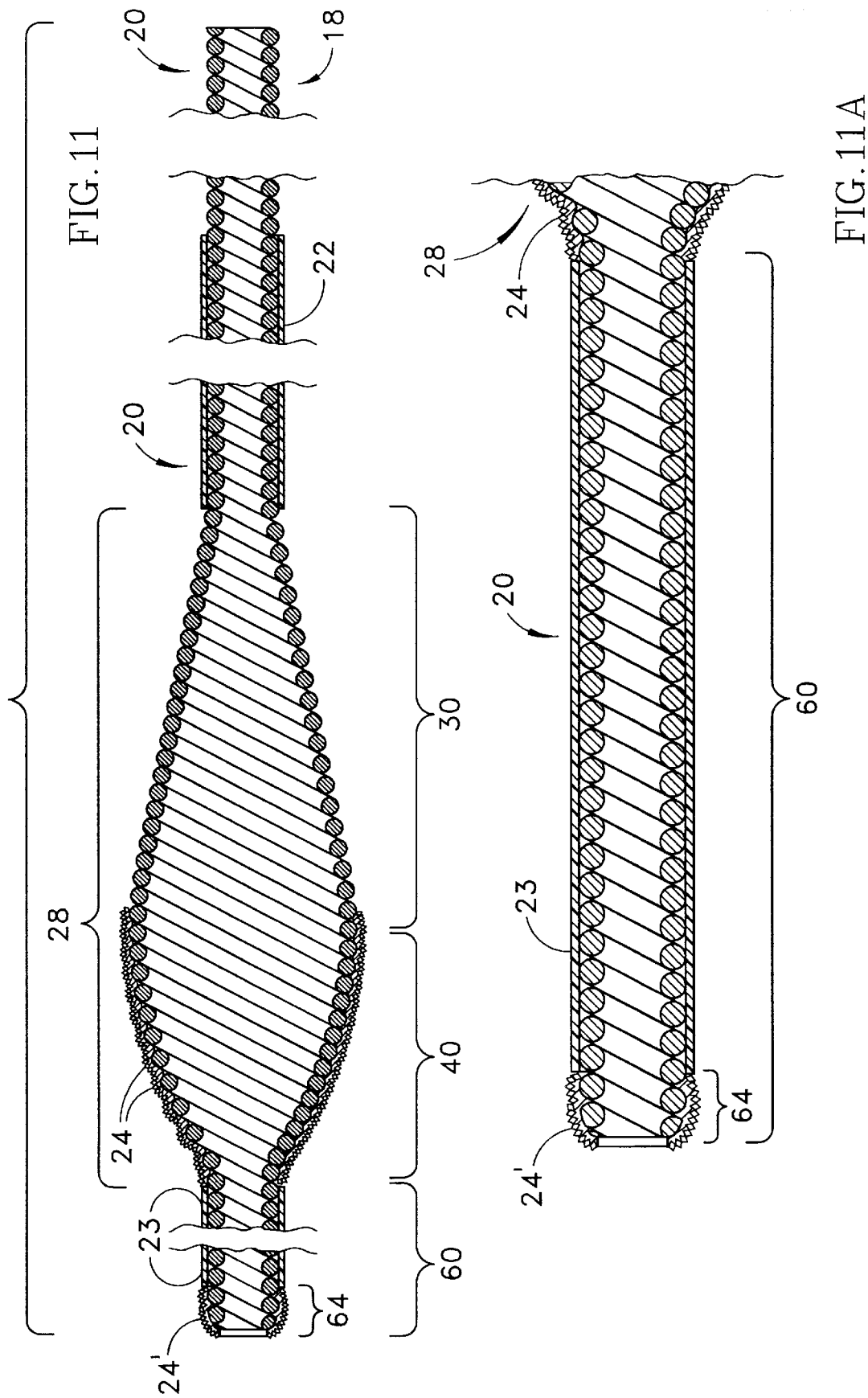
FIG. 11 is a broken-away, longitudinal cross-sectional view of a modified embodiment of the invention having a layer of tubing covering the section of the drive shaft in between the two abrasive segments of the atherectomy device.

FIGS. 11 and 11A depict an embodiment similar to FIGS. 9 and 9A, but with the addition of a thin, flexible, low friction sheath or coating 23 encasing at least a substantial portion of the distal section 60 between the abrasive material 24 of the enlarged diameter section 28 and the abrasive material 24' of the distal end segment 64. The sheath or coating 23 covering the substantial portion of the distal section 60 of the drive shaft 20 may be made from the same material as the sheath or coating 22 covering the portion of the drive shaft 20 immediately proximal to the enlarged diameter tissue removal section 28. For this purpose applicants have successfully utilized heat shrinkable polytetrafluoroethylene tubing.

FIGS. 12–18 depict various embodiments of the atherectomy device of the invention in which the diameters of certain portions of the drive shaft 20 (other than the enlarged diameter tissue removal section 28) are reduced. Reduced diameter segments of the drive shaft 20 can be utilized to function as a bearing for rotation of the drive shaft about a guide wire. The reduced clearance between the guide wire and the inner surface of the reduced diameter segment is less than in other portions of the drive shaft and is intended to reduce vibrations of the enlarged diameter section and facilitate smooth rotation of the drive shaft and its enlarged diameter section about the guide wire when the atherectomy device is rotated at high speeds.

Figure 12:
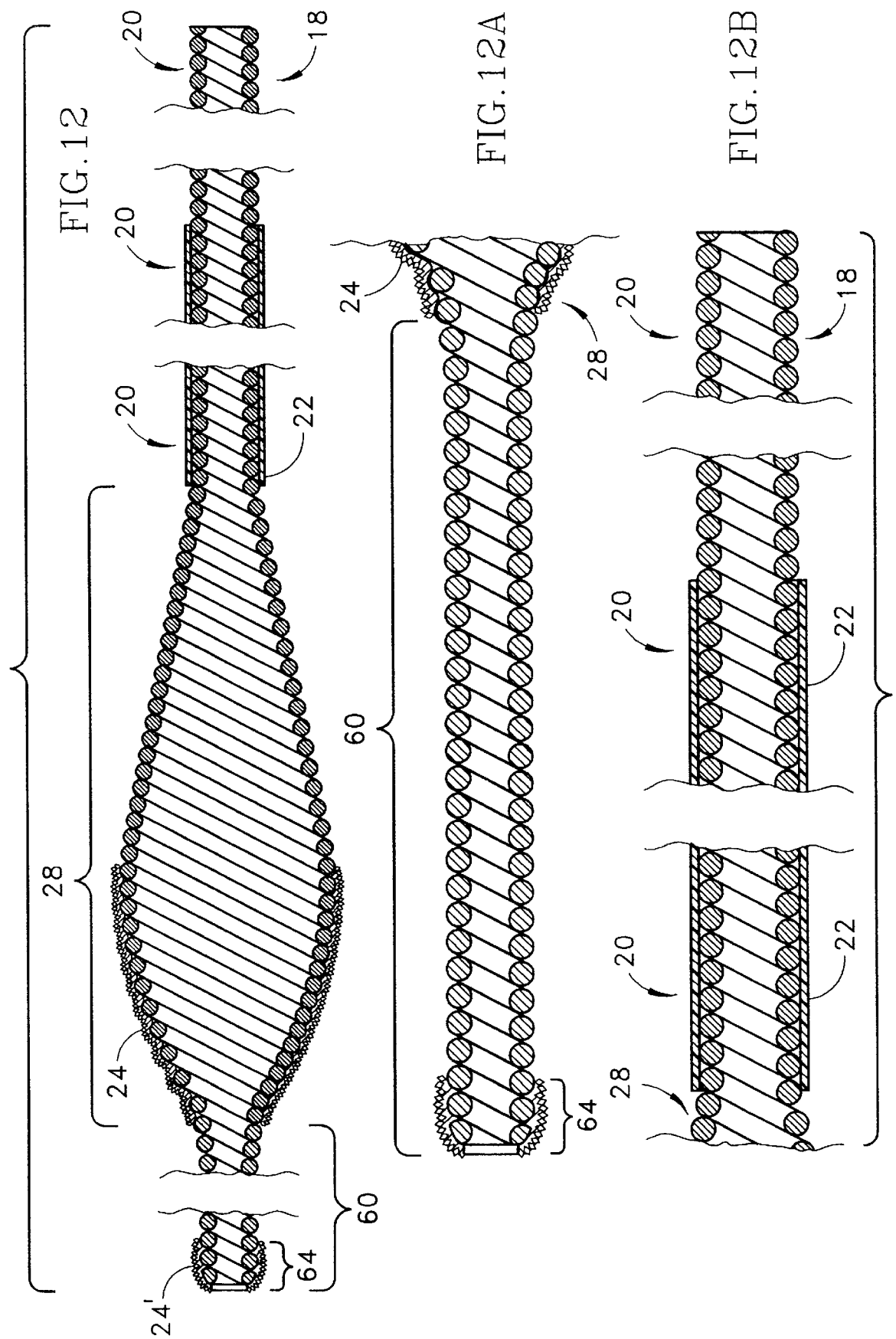
FIG. 12 is a broken-away, longitudinal cross-sectional view of a modified embodiment of the invention having a distal section with a diameter smaller than the diameter of the proximal section of the atherectomy device.
Figure 13:
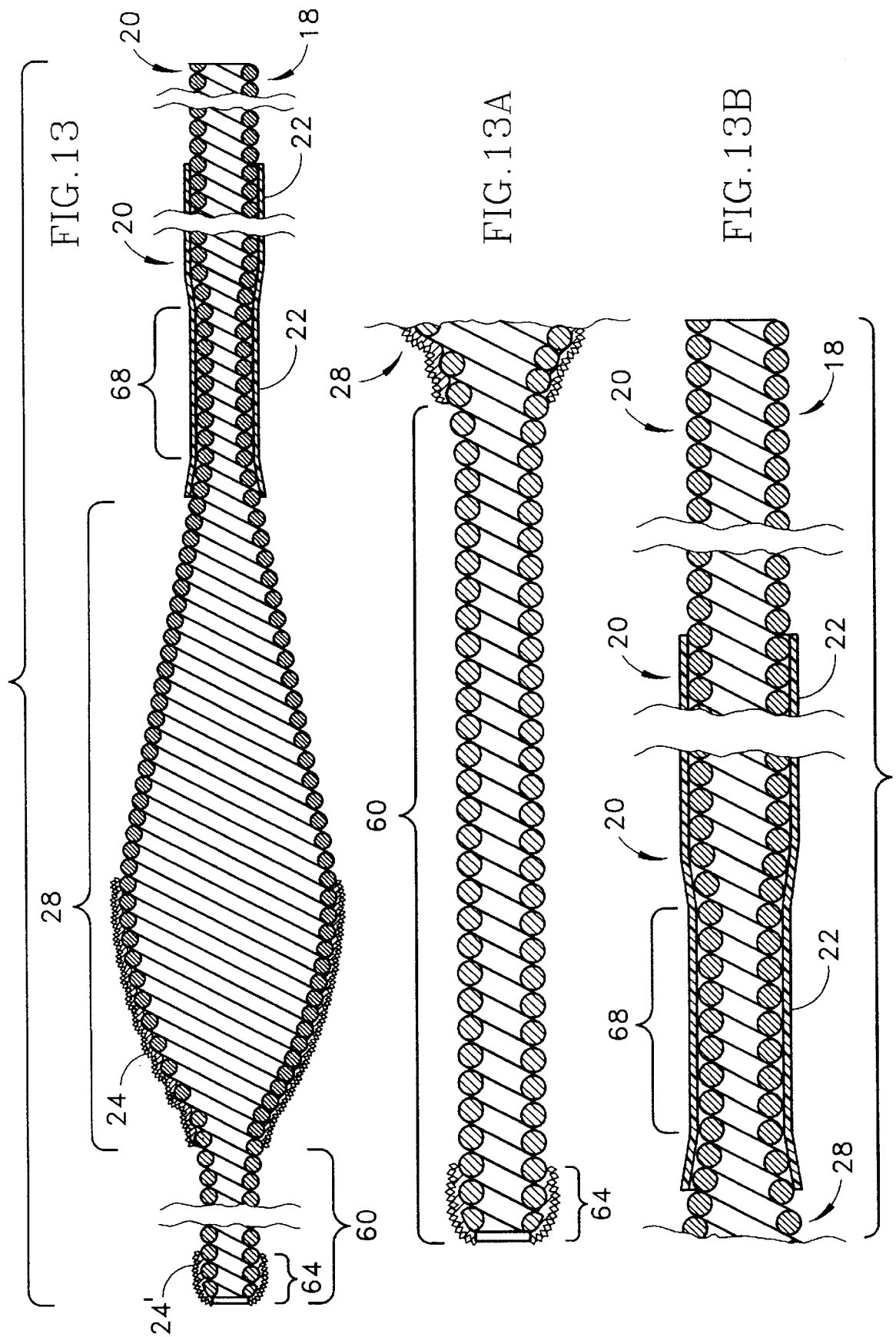
FIG. 13 is a broken-away, longitudinal cross-sectional view of a modified embodiment of the invention having a distal section with a reduced diameter, and a single reduced diameter segment located proximally of the enlarged diameter tissue removal section.

In the embodiment depicted in FIGS. 12, 12A and 12B, the inner and outer diameters of the distal section 60 of the drive shaft 20 are smaller than the corresponding inner and outer diameters of the section of the drive shaft proximal to the enlarged diameter section 28. In FIGS. 13, 13A and 13B the inner and outer diameters of the distal section 60 of the drive shaft 20 are similarly reduced, and there is also a short segment 68, just proximal to the enlarged diameter section 28, which has reduced inner and outer diameters.

Figure 14:
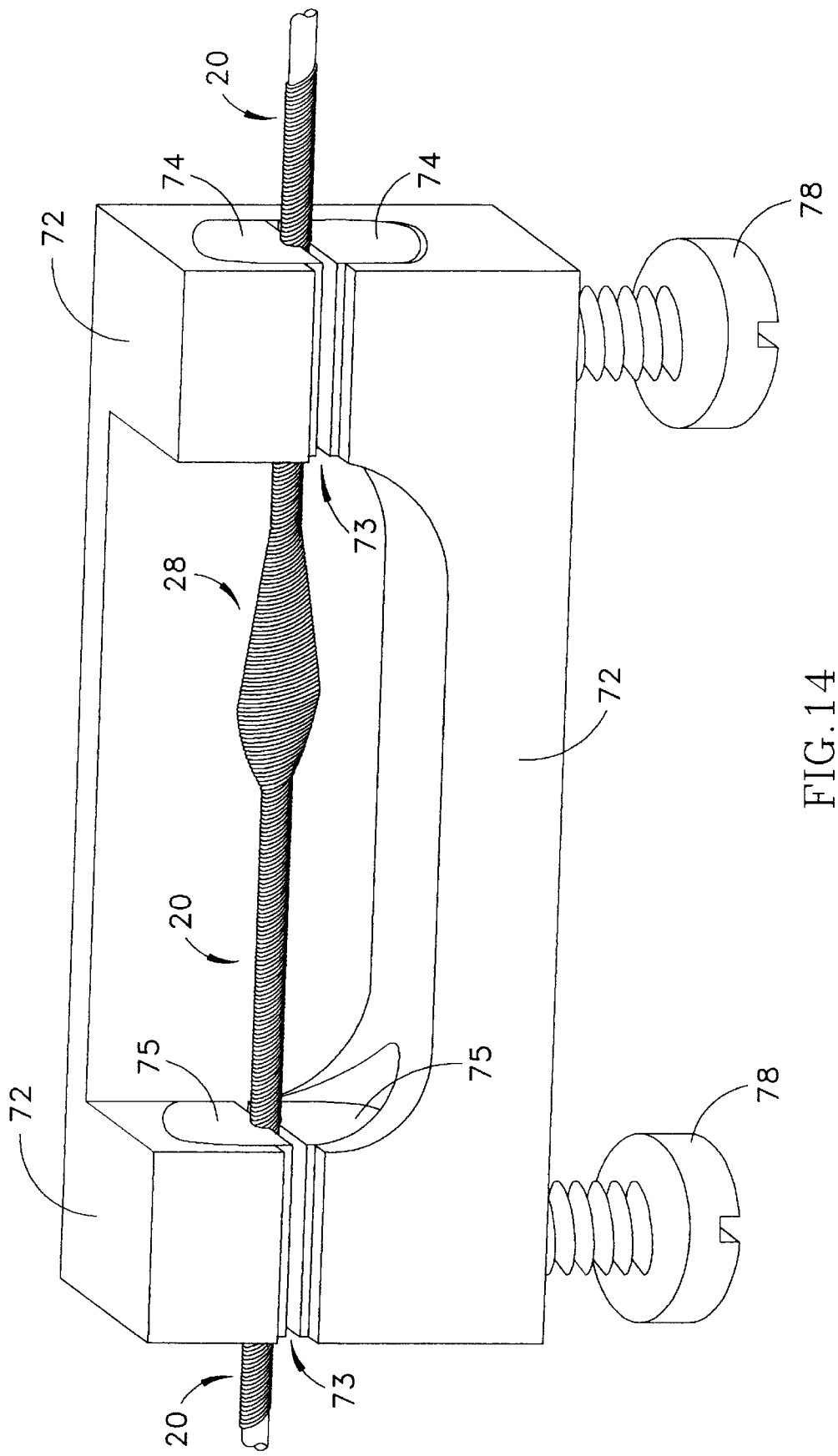
FIG. 14 is a perspective view of a clamp used in manufacturing the rotational atherectomy device shown in FIG. 13, which has a distal section with a reduced diameter, and a single reduced diameter segment located proximally of the enlarged diameter tissue removal section.

FIGS. 14–15 illustrate the use of a clamp in manufacturing the rotational atherectomy device of FIG. 13. The particular clamp shown in FIGS. 14–15 is used to manufacture the specific rotational atherectomy device depicted in FIG. 13, but it will be understood that variations on this clamp may be utilized to make any of the various embodiments depicted in FIGS. 12–13, as well as FIGS. 17–18, described below.

Referring to FIGS. 14–15, the clamp includes a clamp frame 72 with a slot 73, two sets of clamping blocks 74 and 75, and a pair of set screws 78. After the drive shaft wires have been wound about a suitably shaped mandrel (such as the mandrel depicted in FIG. 8) and before the winding tension on the wires has been released, the clamp 72 is secured on the drive shaft at the appropriate location. This is accomplished by first passing the drive shaft through the slot 73 in the clamp frame 72, next positioning the clamping blocks 74 and 75 about the drive shaft 20 and moving them into the clamp frame 72, and finally tightening set screws 78 to firmly clench the drive shaft with its enlarged diameter tissue removal section 28 between the clamping blocks 74 and 75. Once the set screws 78 are tightened, the winding tension on the drive shaft wires may be released. Those portions of the drive shaft wires not captured by the clamp will unwind to a diameter slightly larger than the mandrel, but the clamp will prevent such unwinding for the entire portion of the drive shaft located between the two sets of clamping blocks 74 and 75.

FIG. 14A illustrates in longitudinal cross-section how the drive shaft 20 is clenched by clamping blocks 74 and 75. In FIGS. 14B and 15 the portions of the drive shaft not captured by the clamp are shown as having unwound to a diameter larger than the diameter of the portion captured by the clamp. FIGS. 14A and 14B, however, significantly exaggerate the degree of unwinding—typically the outer diameter of the drive shaft, as a result of unwinding, will expand only about 1% to about 10%.

Once the clamp has been secured to the drive shaft and the portions of the drive shaft not captured by the clamp are allowed to unwind to a slightly larger diameter, then the section of the drive shaft which is distal to the enlarged diameter section 28, the enlarged diameter tissue removal section 28 itself, and about 80 mm of the drive shaft 20 proximal to the enlarged diameter tissue removal section 28 are heat treated (as described above) to give the wires of these portions of the drive shaft the desired "set." After the assembly has cooled, the clamp may be removed. The drive shaft then may be further processed as described above (including removal of the mandrel, second heat treatment and electropolishing).

The reduced diameter distal section 60 (i.e., the portion of the drive shaft 20 distal to the enlarged diameter section 28) preferably is about 10–12 mm long, and may be formed by trimming off the drive shaft 20 proximally to the area (or in the area) where the distal set of clamping blocks 75 was located.

Similar techniques can easily be utilized to produce one or more reduced diameter segments 68 at the desired locations on the drive shaft 20.

Figure 16:
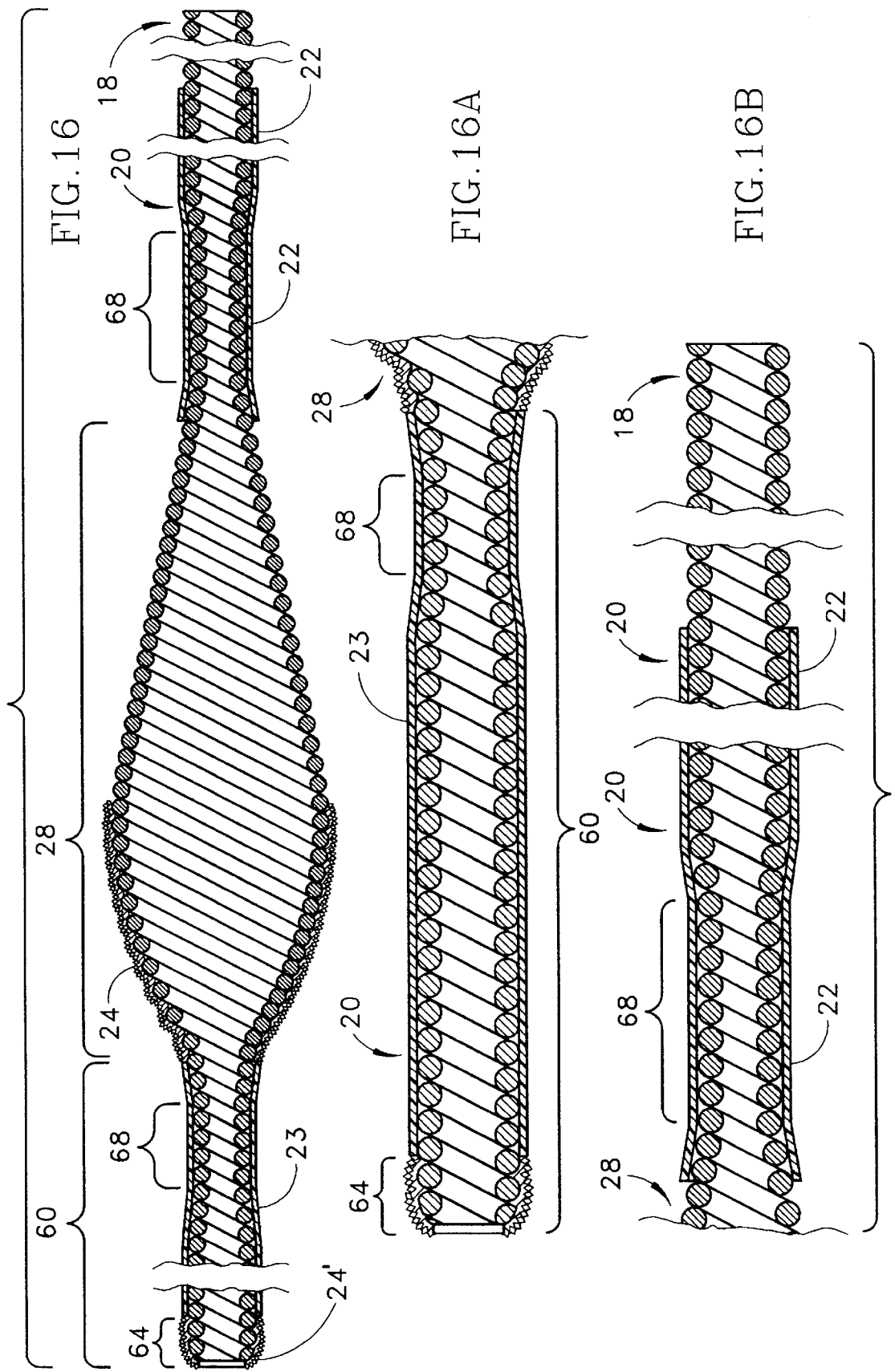
FIG. 16 is a broken-away, longitudinal cross-sectional view of a modified embodiment of the invention with a distal section having a segment with a reduced diameter, and a similar reduced diameter segment located proximally of the enlarged diameter tissue removal section.

FIGS. 16, 16A and 16B depict another rotational atherectomy device in which most of the length of the relatively long distal section 60 has inner and outer diameters equal to the inner and outer diameters of most of the length of the drive shaft 20, except for a relatively short reduced diameter segment 68 located just distal to the enlarged diameter section 28. The rest of the atherectomy device depicted in FIGS. 16, 16A and 16B does not differ from the device depicted in FIGS. 13, 13A and 13B. As a result, the atherectomy device in FIGS. 16, 16A and 16B has two relatively short reduced diameter segments 68, one being located just proximal to the enlarged diameter section 28, and the other being located just distal to the enlarged diameter section 28.

Figure 17:
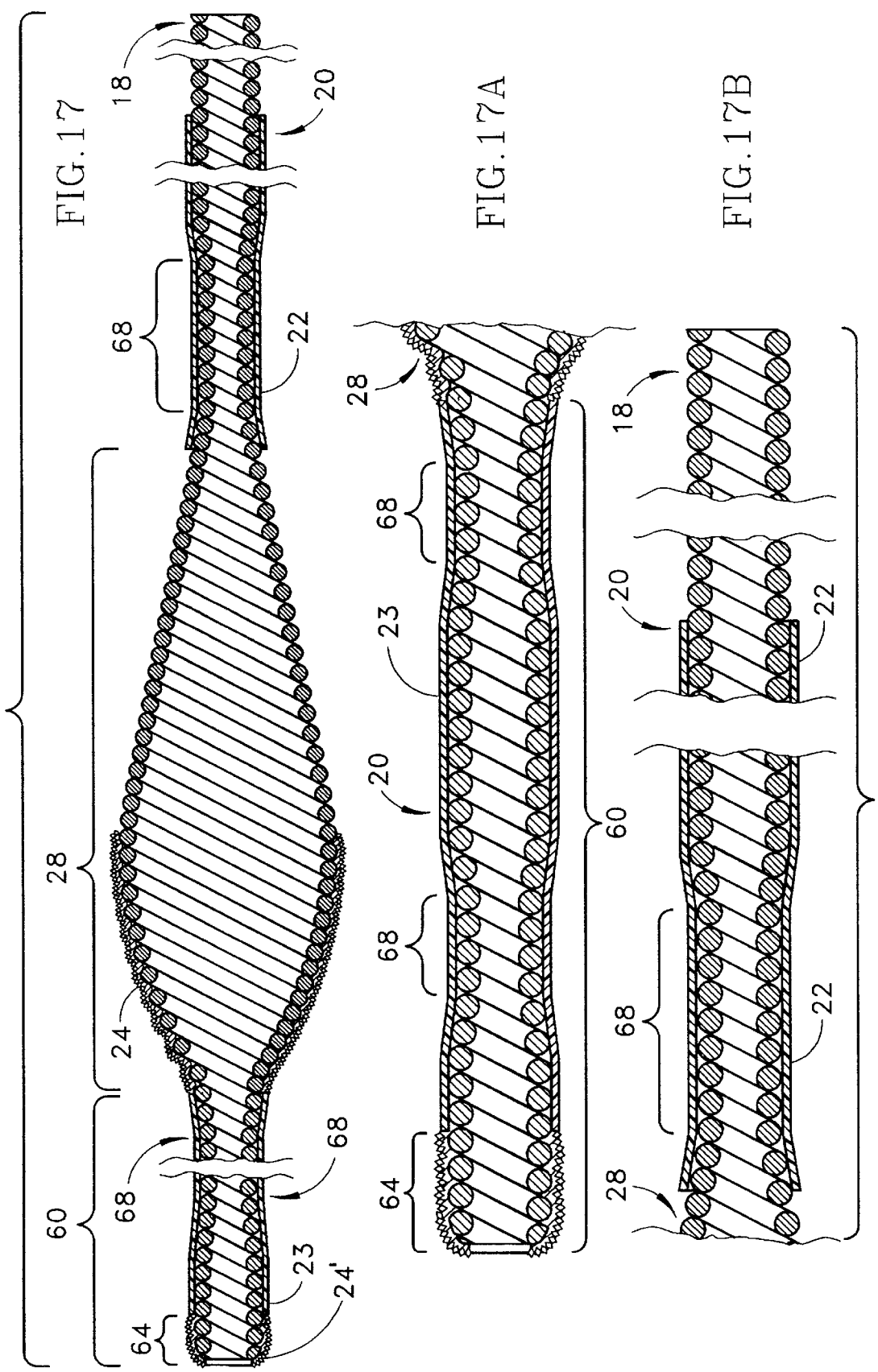
FIG. 17 is a broken-away, longitudinal cross-sectional view of a modified embodiment of the invention with a distal section having two segments with a reduced diameter, and a similar reduced diameter segment located proximally of the enlarged diameter tissue removal section.
Figure 18:
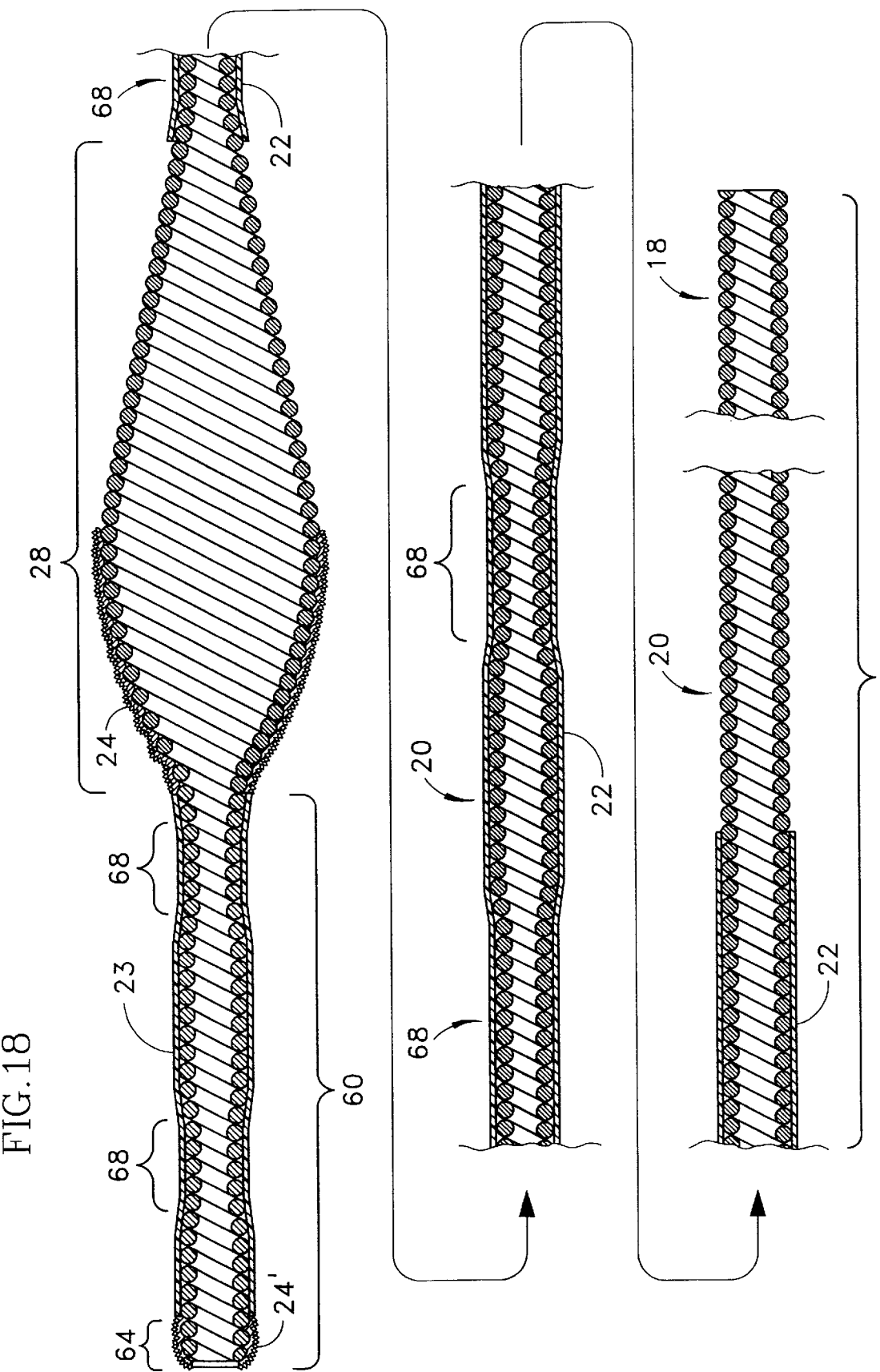
FIG. 18 is a broken-away, longitudinal cross-sectional view of a modified embodiment of the invention with a distal section having two segments with a reduced diameter, and two similar reduced diameter segments located proximally of the enlarged diameter tissue removal section.

FIGS. 17, 17A and 17B depict a similar embodiment having two reduced diameter segments 68 distal to the enlarged diameter tissue removal section 28, and one reduced diameter segment 68 just proximal to the enlarged diameter section 28. FIG. 18 depicts yet another embodiment, this one having two reduced diameter segments 68 distal to the enlarged diameter section 28, and two reduced diameter segments 68 proximal to the enlarged diameter section 28.

Selection of the number and location of the reduced diameter segments can be made based on the performance characteristics desired. Preferably at least one of such reduced diameter segments is located within about one inch from the enlarged diameter tissue removal section 28, and most preferably within about a quarter inch from such enlarged diameter tissue removal section 28.

Figure 19:
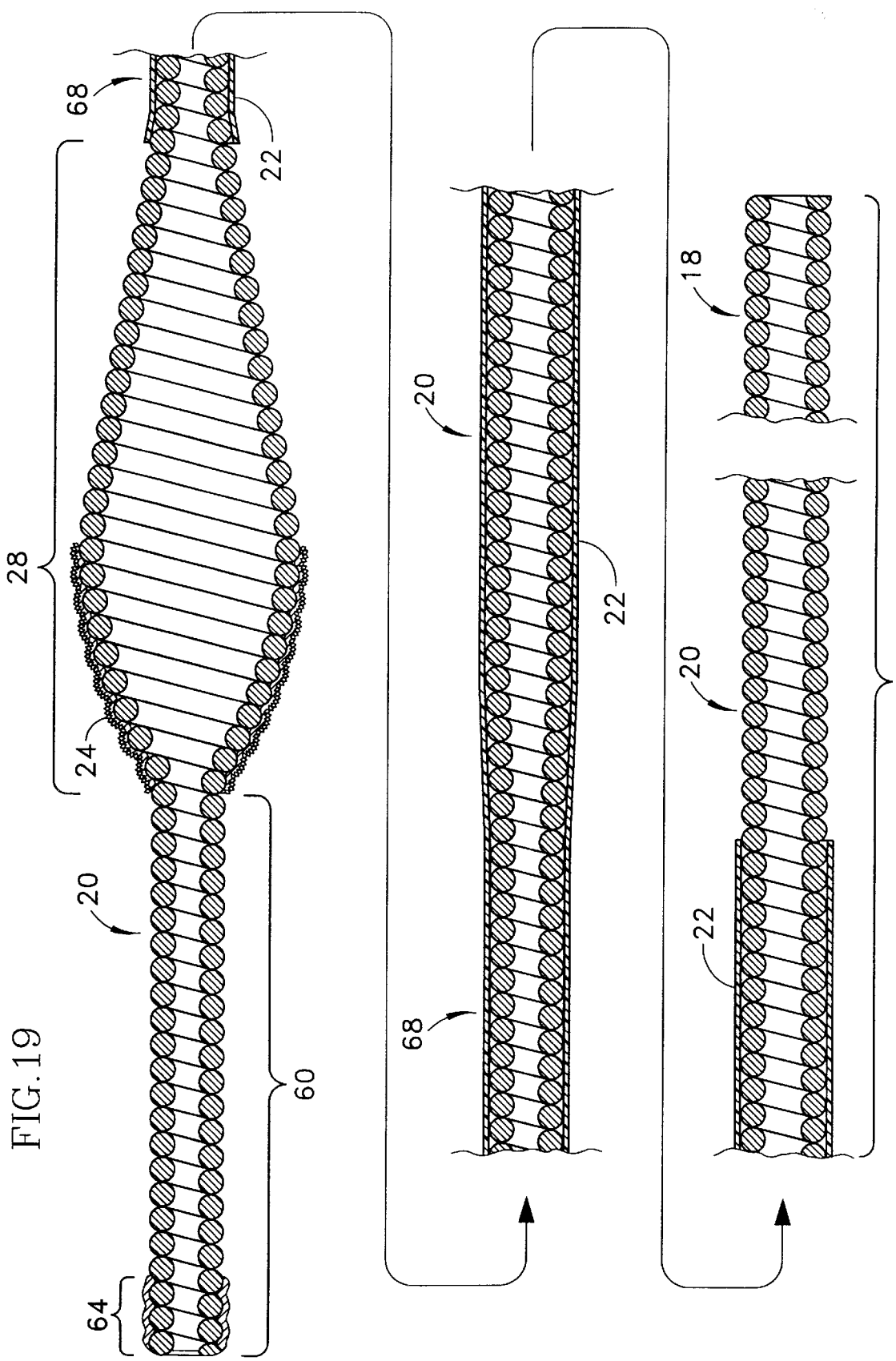
FIG. 19 is a broken-away, longitudinal cross-sectional view of a modified embodiment of the invention similar to FIG. 13, but wound from a single strand of wire.

FIG. 19 shows an embodiment generally similar to the embodiment depicted in FIGS. 13—13B—5both the embodiment of FIG. 13 and the embodiment of FIG. 19 include a drive shaft 20 having a distal section 60 with reduced inner and outer diameters, as well as a short segment 68, just proximal to the enlarged diameter section 28, which also has reduced inner and outer diameters. The embodiment of FIG. 19 differs, however, in that it is manufactured from a single strand of wire. Use of one wire strand (as opposed to multiple wire strands) facilitates manufacture of the device by spring coiling machine technology, such as that which is commercially available from, e.g., WMC WAFIOS Machinery Corp. of Branford, Conn. (affiliated with WAFIOS Maschinenfabrik GmbH & Co., of Reutlingen, Germany). Spring coiling machines are capable of coiling wire without the use of a mandrel—hence, a wide variety of shapes can be coiled without the need to construct or remove a mandrel. The embodiment of FIG. 19 utilizes slightly larger diameter wire (e.g., about 0.009–0.010 inch diameter, whereas the embodiment of FIG. 13 can be made from wire as thin as about 0.006–0.007 inches). This gives the drive shaft 20 (excluding the enlarged diameter tissue removal section 28) of the device of FIG. 19 a slightly larger outer diameter than the corresponding portions of the drive shaft of the device of FIG. 13, but both devices can be manufactured with drive shafts having the same inner diameters.

Figure 20:
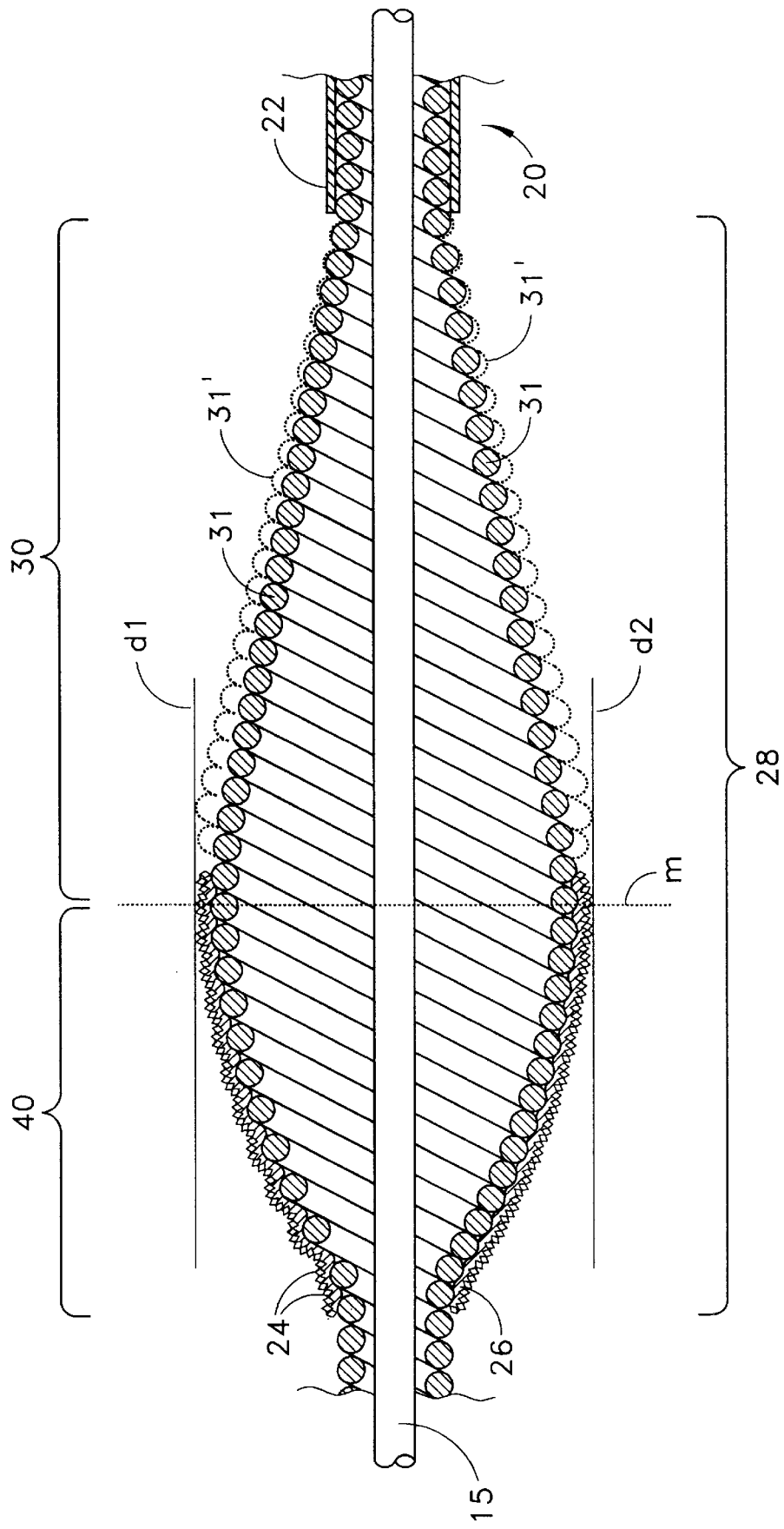
FIG. 20 is a broken-away, longitudinal cross-sectional view of an atherectomy device of the invention, showing both the extent of coverage by the abrasive material of the enlarged diameter tissue removal section of the rotational atherectomy device, and a moved position of the wire turns of the enlarged diameter tissue removal section of the device when the wire turns are unwinding under load.

FIGS. 20–23 show several related embodiments of the invention which illustrate a unique performance characteristic of the rotational atherectomy device of the invention. In FIG. 20 the enlarged diameter tissue removal section 28 of the rotational atherectomy device has a maximum diameter (measured at line "m") equal to the distance from line $d_1$ to line $d_2$. The wire turns 31 of the proximal, generally conical portion 30 of the drive shaft's enlarged diameter section 28 are shown in a moved position 31', the wire turns 31 expanding to this position when they unwind under rotational load during use of the atherectomy device. Rotational load on the drive shaft 20 in general (and on the generally conical portion 30, in particular) increases rapidly each time when the rotating abrasive segment of the drive shaft (i.e., the portion of the drive shaft covered with abrasive material 24) engages stenotic tissue and consequently the torque applied to the proximal end of the drive shaft by the turbine of the atherectomy device is opposed by the torque of the frictional forces applied to the abrasive segment of the drive shaft when it engages stenotic tissue.

In the embodiment of FIG. 20, the abrasive coating 24 covers not only the entire distal portion 40 of the enlarged diameter section 28 of the drive shaft, but also a small portion of the enlarged diameter section 28 which is proximal to line "m". Extending the coverage of the abrasive coating 24 proximally of the line "m" results in a more substantial portion of the enlarged diameter tissue removal section 28 being usable for tissue removal.

In FIG. 20, the physical configuration of the enlarged diameter section 28 is designed so that, under load, wire turns 31 of the proximal, generally conical portion 30 of the enlarged diameter section 28 unwind to the extent that one or more of the wire turns near the distal end of the generally conical portion 30 reach a diameter equal to the "at rest" maximum diameter of the enlarged diameter tissue removal section 28 (measured at line "m"). Typically it is not the most distal wire turn(s) of the generally conical portion 30 of the drive shaft that unwind most. This is because the most distal wire turn of the generally conical portion 30 is located immediately proximally to the abrasive segment of the drive shaft. Since the wire turns of the abrasive segment of the drive shaft are preferably fixed to each other, they are incapable of unwinding. The wire turns of the abrasive segment are preferably bonded to one another by the binder 26 which secures the abrasive coating 24 to the wire turns of the drive shaft.

Figure 21:
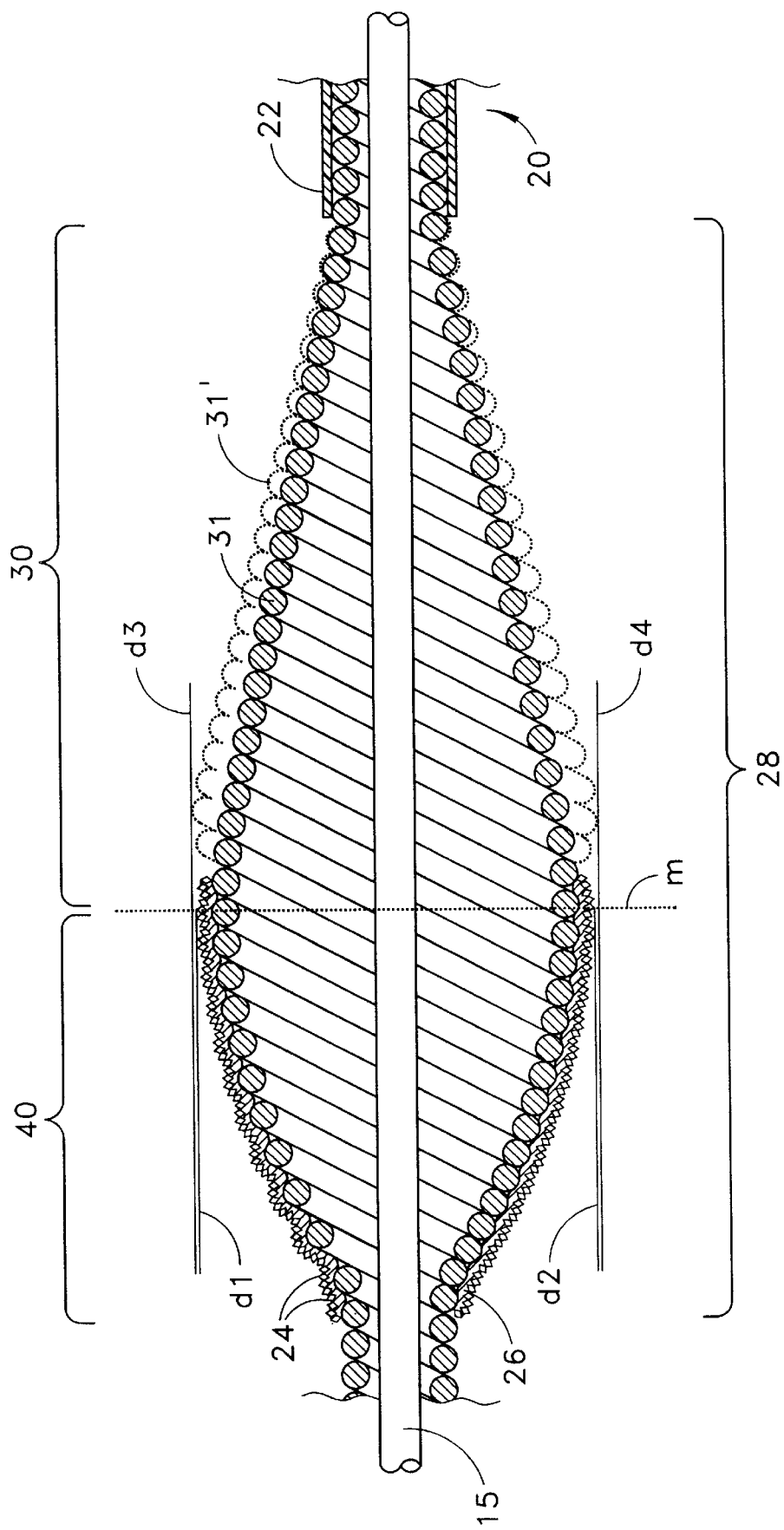
FIG. 21 is a broken-away, longitudinal cross-sectional view of another embodiment of an atherectomy device similar to FIG. 20, the wire turns, in their moved position, being depicted as unwinding to a slightly larger diameter.

FIG. 21 illustrates a modified embodiment in which the physical configuration of the enlarged diameter section 28 is designed so that under typical load conditions at least some of the wire turns 31 of the proximal, generally conical portion 30 of the enlarged diameter section 28 unwind to a diameter slightly larger than the "at rest" maximum diameter of the enlarged diameter section 28 (again, measured at line "m"). In FIG. 21, the maximum diameter of the wire turns in the moved position 31' is equal to the distance from line $d_3$ to line $d_4$.

This expansion under load of some of the wire turns of the proximal, generally conical portion 30 of the enlarged diameter tissue removal section 28 to a diameter equal to or slightly larger than the "at rest" maximum diameter of the enlarged diameter section 28 tends to limit lateral (i.e., radial) tissue removal by the abrasive coating 24 to a diameter essentially equal to the maximum "at rest" diameter of the enlarged diameter section 28. That is, expansion of the generally conical portion 30 provides a lateral (i.e., radial) shield to prevent adjacent tissue from contacting the abrasive material 24 located immediately distally of the expanded wire turns of the generally conical portion 30. At any time the unwinding of the wire turns of the generally conical portion 30 may be significantly reduced or eliminated by stopping the rotation of the turbine (thereby eliminating torque applied to the proximal end of the drive shaft) or by slightly withdrawing the drive shaft 20 (thereby reducing the torque of frictional forces between the abrasive coating 24 and the stenotic tissue). Return of the wire turns of the generally conical portion 30 to their normal "at rest" diameter facilitates withdrawal of the enlarged diameter tissue removal section 28 from the artery once the stenosis has been opened; desirably the drive shaft 20 should continue to be rotated while it is withdrawn, though preferably at a significantly reduced rotational speed.

The degree of unwinding of the wire turns is dependent upon a number of parameters including the diameter of the wire, the material from which the wire is made, the maximum diameter of the enlarged tissue removal section 28, and the rotational load applied to the drive shaft. The rotational load applied to the drive shaft in turn depends on the torque of the turbine and the drop in rotational speed which is permitted when the rotating abrasive segment engages stenotic tissue to be removed. Preferably all these parameters are adjusted so that the desired amount of unwinding of the wire turns is achieved when the tissue removal section 28 of the drive shaft is gently advanced against the stenotic tissue. In a device designed to operate, e.g., at a rotational speed in the range of 150,000–190,000 rpm (devices having smaller diameter tissue removal sections being operated at the higher end of this range, and devices having larger diameter tissue removal sections being operated at the lower end of this range) desirably the rotational speed of the drive shaft should not decrease by more than about 5,000 rpm under such gentle advancement against stenotic tissue. Such relatively small drop in the rotational speed of the drive shaft should not produce either excessive heat at the atherectomy site or a substantial increase in the size of the tissue particles removed. This drop in rotational speed, however, allowed Applicants to achieve a practically useful amount of unwinding of the wire turns of the generally conical portion 30 of the drive shaft for drive shafts having enlarged diameter segments 28 with maximum diameters of about 2 mm or larger.

Figure 22:
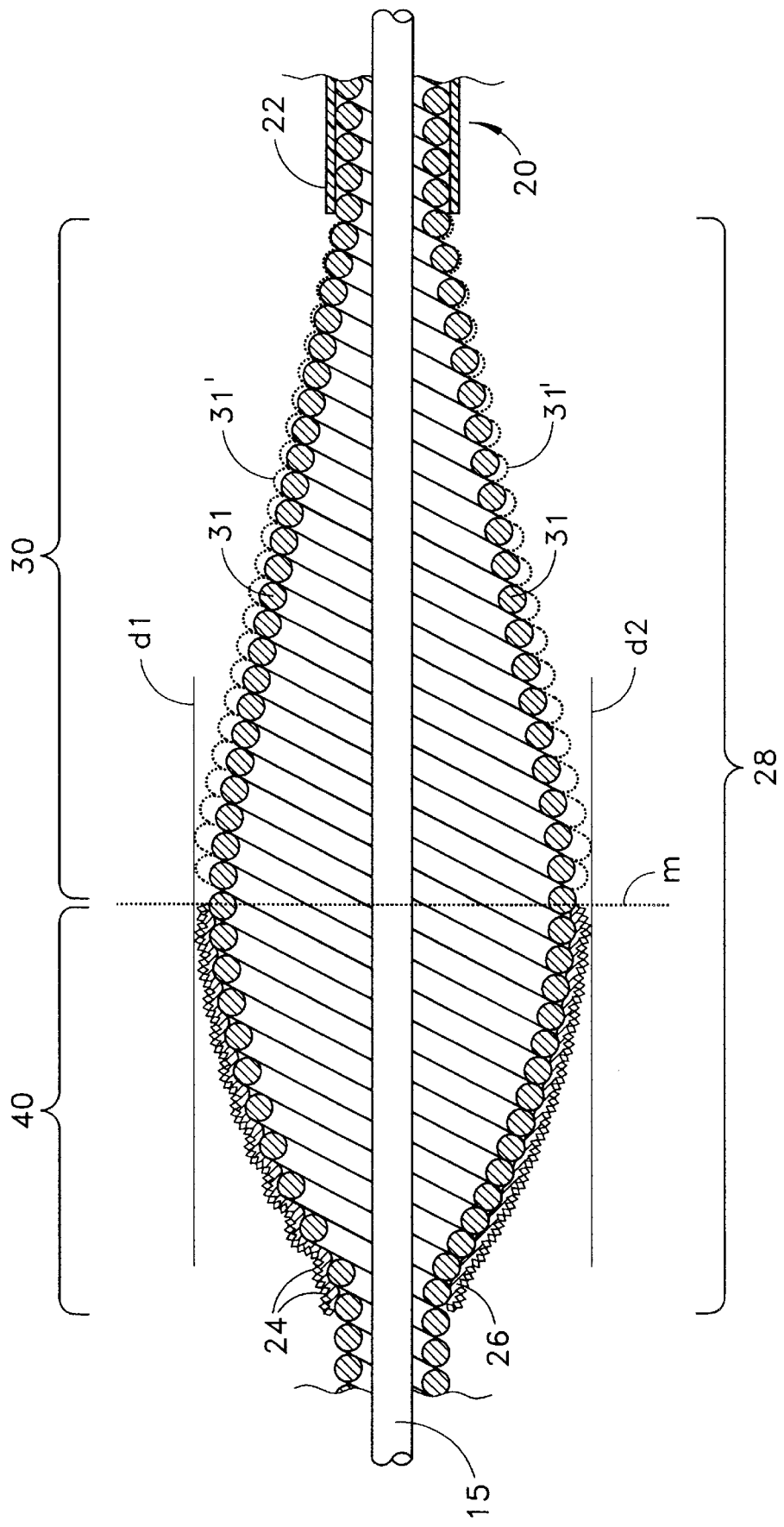
FIG. 22 is a broken-away, longitudinal cross-sectional view of an atherectomy device similar to FIG. 20, with the proximal end of the abrasive segment terminating at the maximum diameter of the enlarged diameter tissue removal section.
Figure 23:
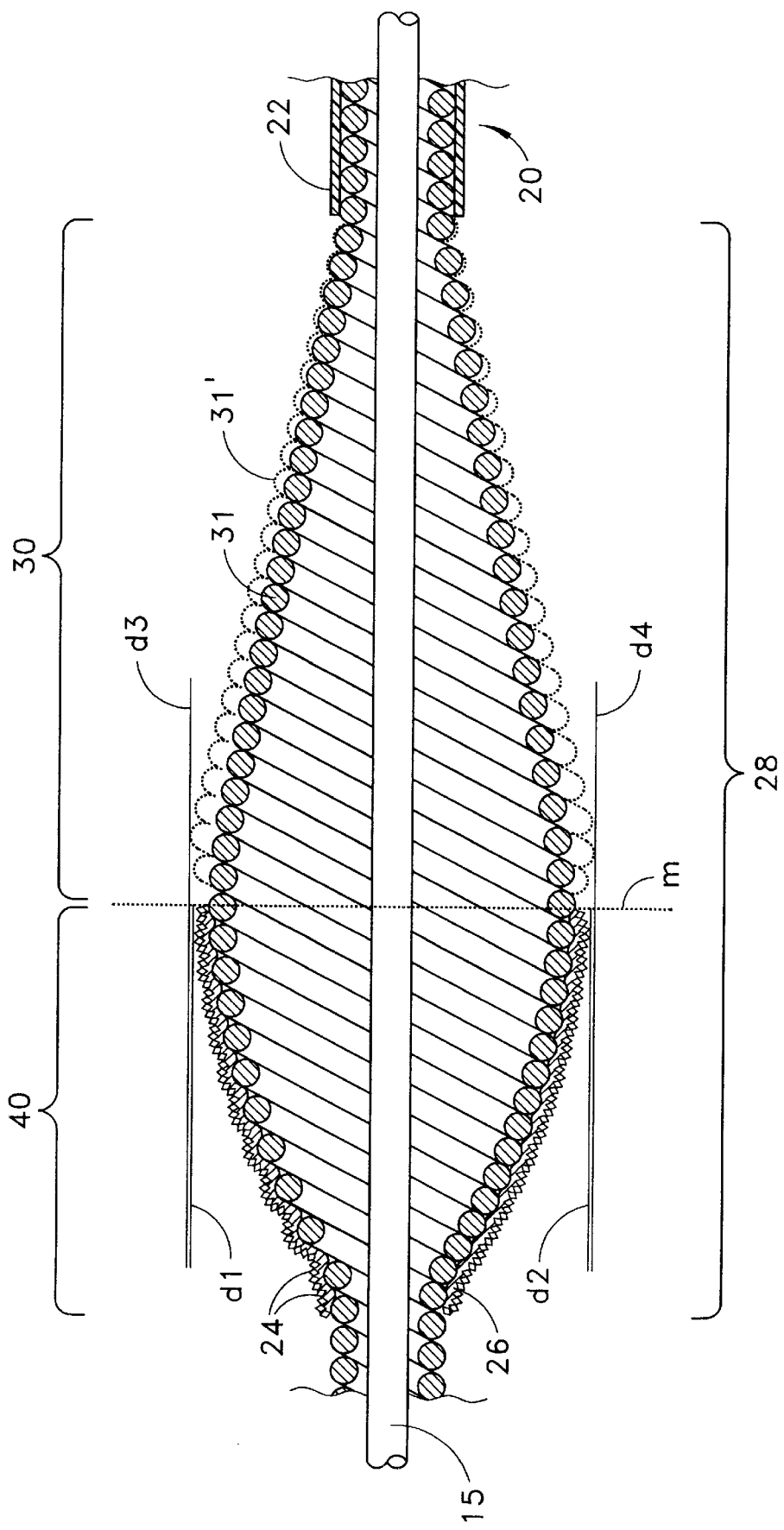
FIG. 23 is a broken-away, longitudinal cross-sectional view of an atherectomy device similar to FIG. 21, with the proximal end of the abrasive segment terminating at the maximum diameter of the enlarged diameter tissue removal section.

FIGS. 22 and 23 are similar to FIGS. 20 and 21, but differ in that the abrasive coating 24 in each of these embodiments covers only the distal portion 40 of the enlarged diameter section 28 of the drive shaft, and does not extend into the proximal generally conical portion 30 of the enlarged diameter section 28 of the drive shaft 20 (i.e., the abrasive coating terminates at line "m", the location of the maximum "at rest" diameter of the enlarged diameter section 28).

Figure 24:
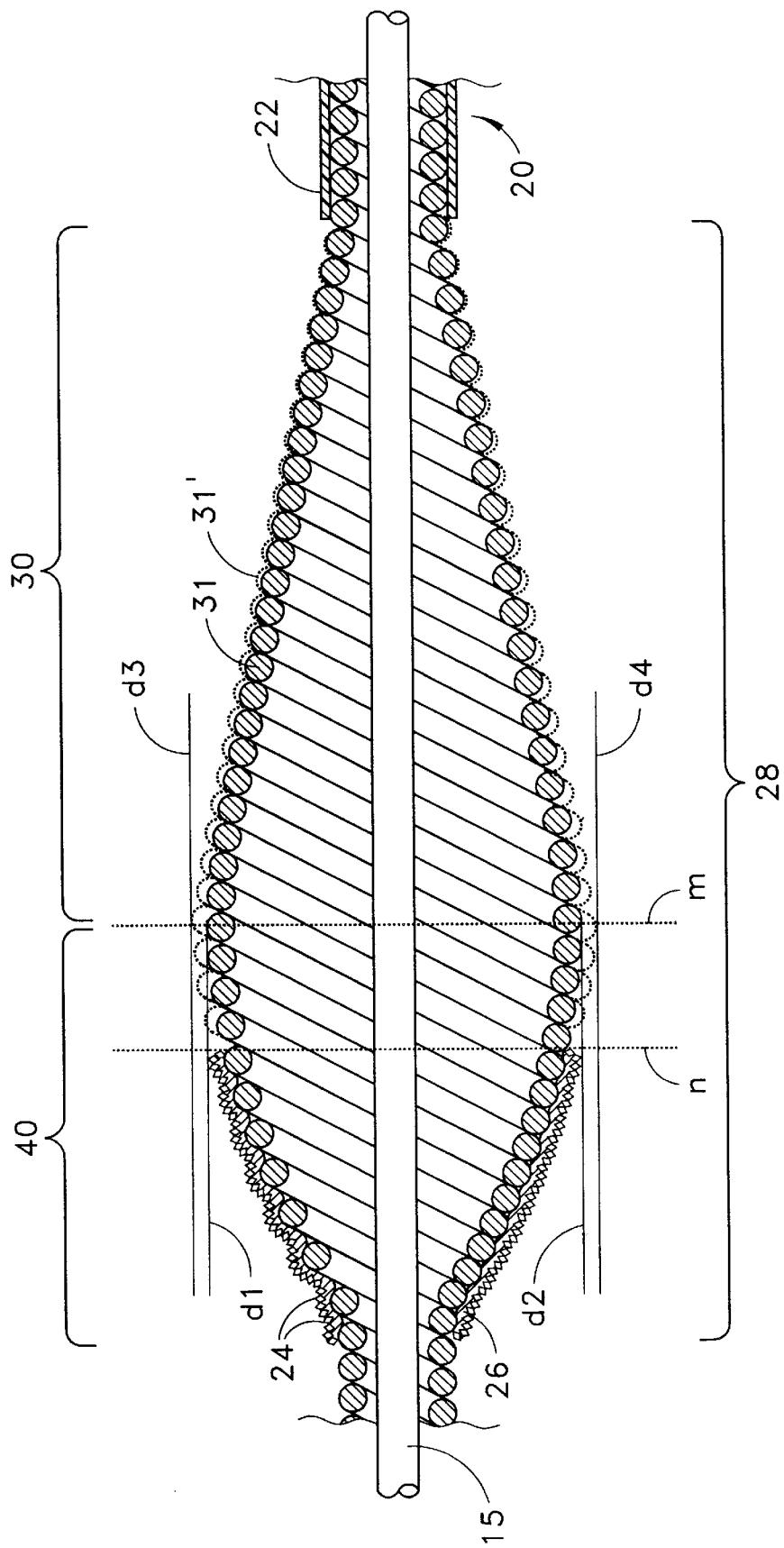
FIG. 24 is a broken-away, longitudinal cross-sectional view of an atherectomy device of the invention, with the proximal end of the abrasive segment terminating distally of the maximum diameter of the enlarged diameter tissue removal section.

FIG. 24 is similar to FIGS. 21 and 23 in that, under typical load conditions, at least some of the wire turns 31 of the proximal, generally conical portion 30 of the enlarged diameter section 28 (and, in the FIG. 24 embodiment, some of the proximal wire turns of the distal portion 40 of the enlarged diameter section 28) unwind to a diameter slightly larger than both the "at rest" maximum diameter of the enlarged diameter tissue removal section 28, and, more importantly, the maximum diameter of the abrasive coating 24. This embodiment differs, however, from FIGS. 21 and 23 in that the abrasive coating 24 in this embodiment covers only part of the distal portion 40 of the enlarged diameter section 28 of the drive shaft. In particular, the abrasive coating covers only a distal part of the enlarged diameter section's distal portion 40, the coating terminating at line "n" on FIG. 24. Because the abrasive coating 24 does not extend proximally beyond line "n", the maximum diameter of the abrasive coating 24 (i.e., the distance from line $d_1$ to line $d_2$, as measured at line "n") is about equal to the maximum "at rest" diameter of the enlarged diameter section 28 (i.e., the distance from line $d_1$ to line $d_2$, as measured at line "m"). Under typical load conditions, however, the wire turns 31 of the enlarged diameter section 28 at line "m" unwind to a diameter slightly larger than the maximum diameter of the abrasive coating 24.

Figure 25:
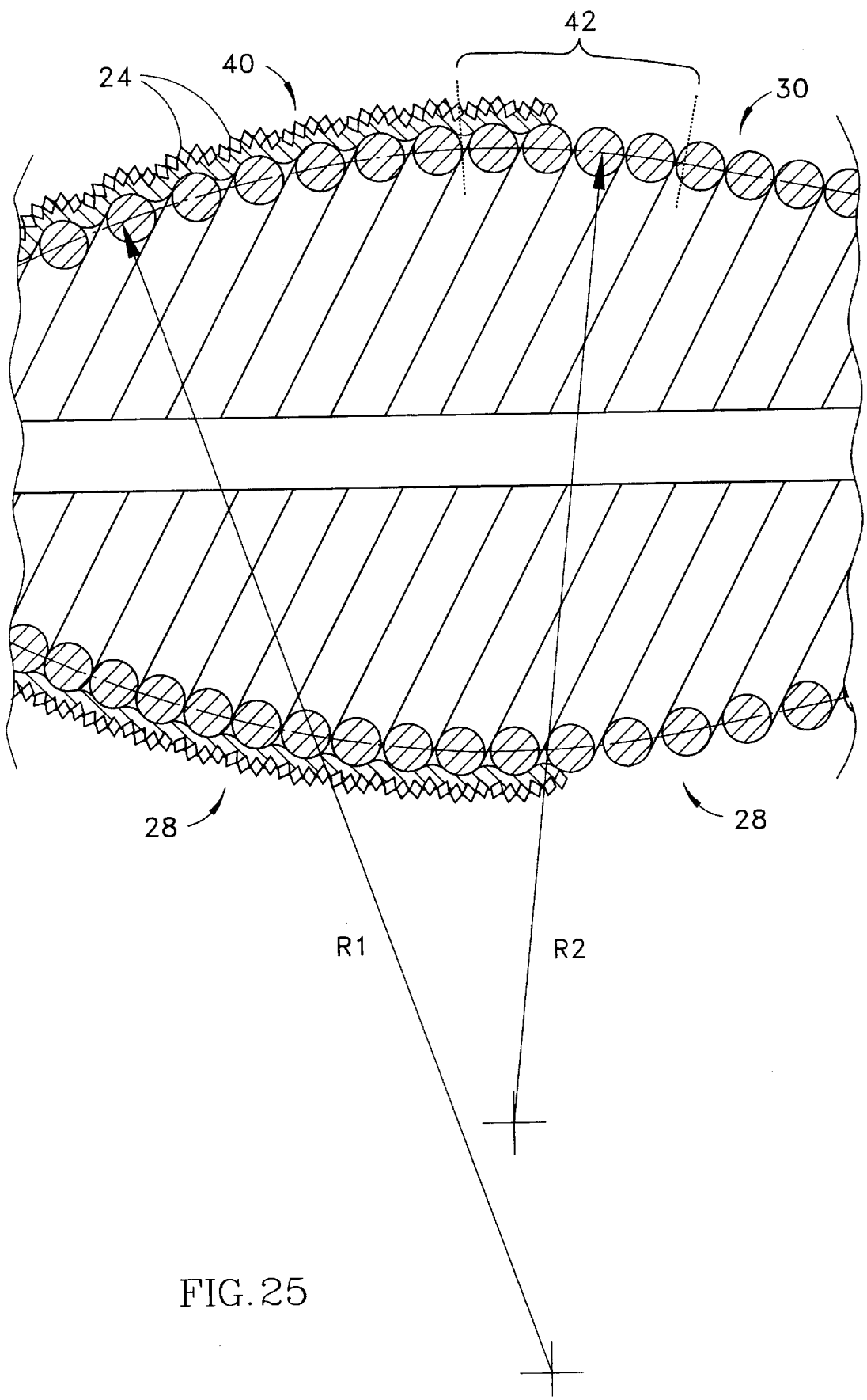
FIG. 25 is an enlarged longitudinal cross-sectional view of a portion of a rotational atherectomy device of the invention, illustrating changes in the longitudinal cross-sectional profile of its enlarged diameter tissue removal section.

FIG. 25 shows in enlarged detail changes in the longitudinal cross-sectional profile of the enlarged diameter tissue removal section 28 of the rotational atherectomy device depicted in FIG. 2. Wire turns of the proximal portion 30 of the tissue removal section 28 have diameters that increase distally at a generally constant rate, thereby forming a generally conical proximal section. Wire turns of the distal portion 40 of the enlarged diameter section 28 have diameters that gradually decrease distally thereby forming a generally convex distal portion 40 having a longitudinal cross-section with a first radius of curvature $R_1$. The enlarged diameter section includes an intermediate transitional portion 42 between the generally conical proximal section and the generally convex distal portion, the transitional portion 42 having wire turns with diameters that gradually decrease proximally, thereby forming a generally convex transitional portion 42 having a longitudinal cross-section with a second radius of curvature $R_2$ which is smaller than the first radius of curvature $R_1$. The transitional portion 42 thus provides a smooth transition from the generally conical proximal portion 30 of the enlarged diameter section 28 to the convex distal portion 40 of the enlarged diameter section 28.

Figure 26:
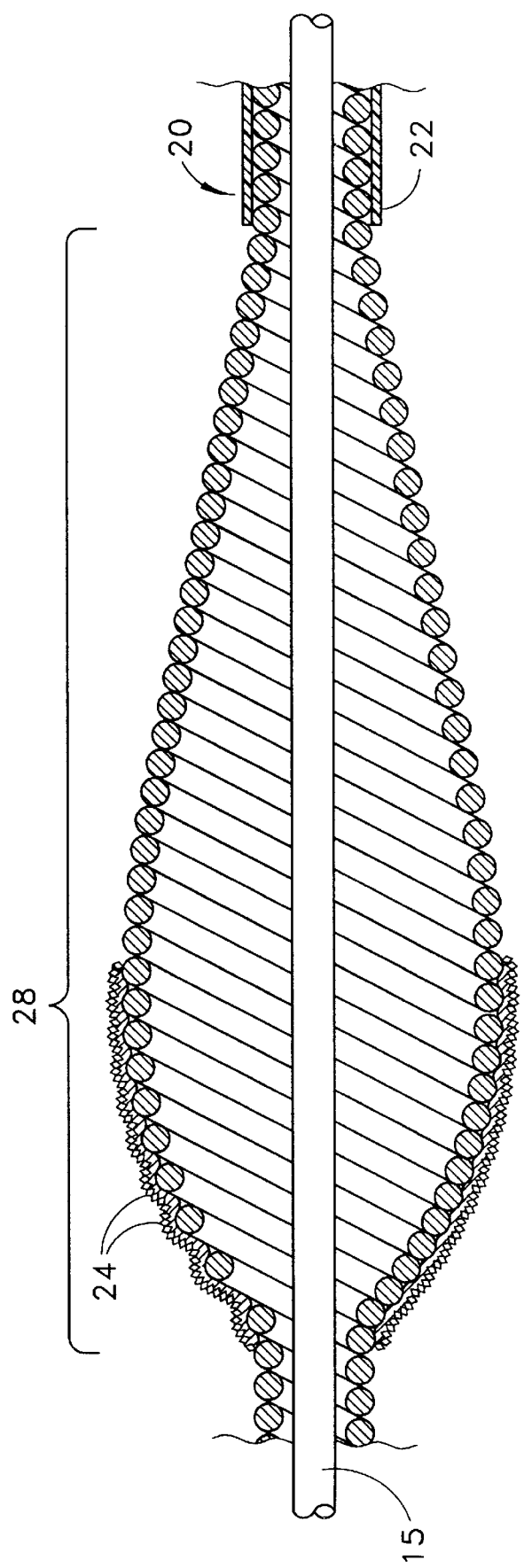
FIG. 26 is a broken-away, longitudinal cross-sectional view of another atherectomy device of the invention, illustrating a slightly different profile of the enlarged diameter tissue removal section.
Figure 27:
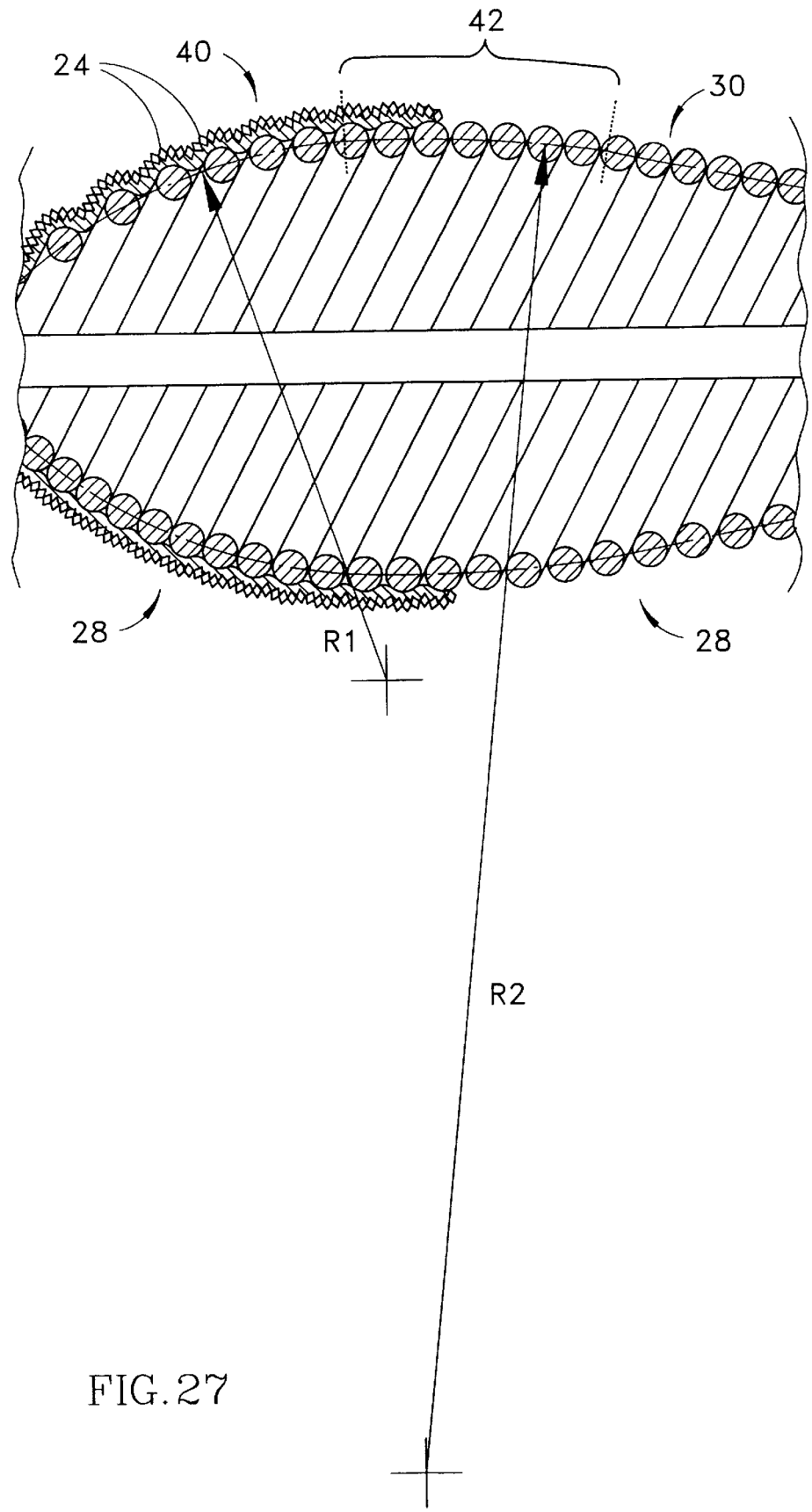
FIG. 27 is an enlarged view of a portion of the atherectomy device of FIG. 26, illustrating the changes in the longitudinal cross-sectional profile of its enlarged diameter tissue removal section.

FIGS. 26 and 27 depict a rotational atherectomy device having an enlarged diameter tissue removal section 28 with a slightly different longitudinal cross-sectional profile. In this embodiment, the first radius of curvature $R_1$ of the distal portion 40 of the tissue removal section 28 is smaller than the second radius of curvature $R_2$ of the intermediate transitional portion 42 of the tissue removal section 28.

Figure 28:
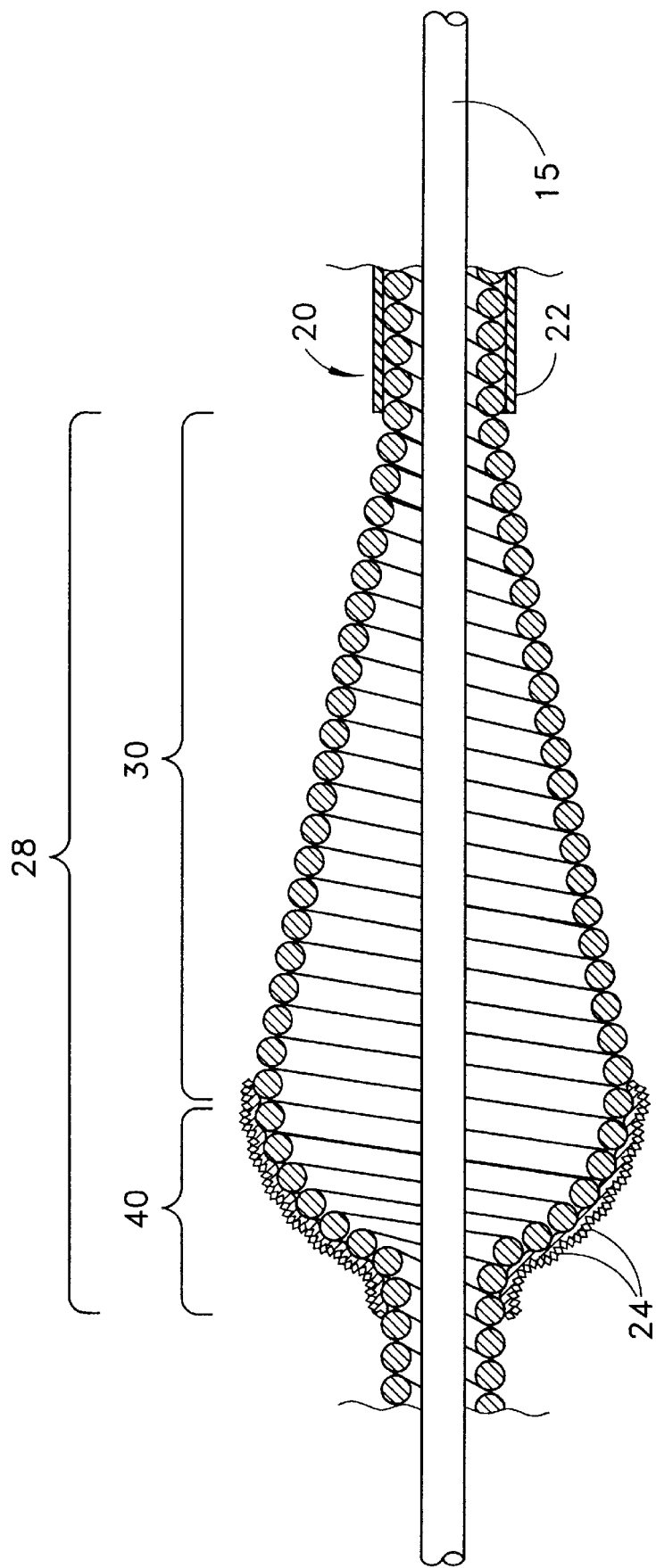
FIG. 28 is a broken-away, longitudinal cross-sectional view of another atherectomy device of the invention, illustrating a different profile of the enlarged diameter tissue removal section.

FIG. 28 depicts an enlarged diameter tissue removal section 28 of a rotational atherectomy device having another different longitudinal cross-sectional profile. In this embodiment, the distal portion 40 of the enlarged diameter section 28 has an essentially hemispherical configuration, directly abutting the proximal conical portion 30 (i.e., there is no intermediate transitional portion).

Figure 29:
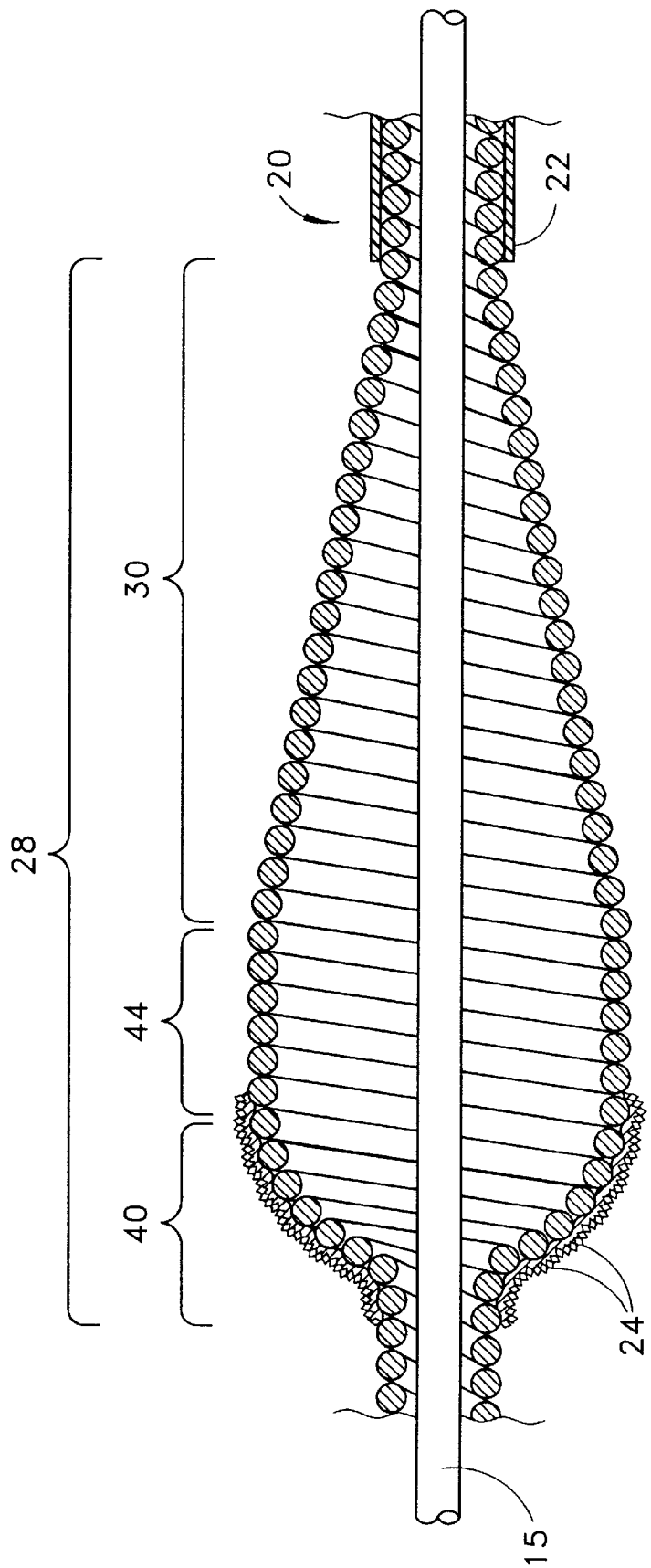
FIG. 29 is a broken-away, longitudinal cross-sectional view of another atherectomy device of the invention, illustrating yet another profile of the enlarged diameter tissue removal section.

FIG. 29 shows yet another variation of the longitudinal profile of an enlarged diameter tissue removal section 28, which employs a generally cylindrical transitional portion 44 between the hemispherical distal portion 40 and the conical proximal portion 30. It will be understood that other variations on these profiles may be readily constructed by one of ordinary skill in the art.

FIGS. 30A and 30B illustrate an advantage of the rotational atherectomy device of the invention. The enlarged diameter tissue removal section 28 of the device in FIG. 30A, e.g., may have a diameter of about 1.5 mm and a length of about 4.1 mm, and the enlarged diameter tissue removal section 28 of the device in FIG. 30B, e.g., may have a diameter of about 2.1 mm and a length of about 6.1 mm. Note that these two enlarged diameter tissue removal sections are generally geometrically proportional to one another, notwithstanding being of different diameters.

The ability to maintain such proportionality permits one to design and select profiles of the tissue removing component based entirely on desired performance characteristics, permitting the profile of the tissue removing component to be scaled up or down without destroying its selected geometry. In contrast, certain prior art devices which physically attach a diamond coated rigid burr to a drive shaft (such as those depicted in U.S. Pat. No. 4,990,134 (Auth)) require certain minimum thickness and length characteristics of the burr in order to assure adequate fixation of the burr to the drive shaft, therefore placing significant constraints on possible design profiles of such tissue removing component of the atherectomy device.

Figure 31A:
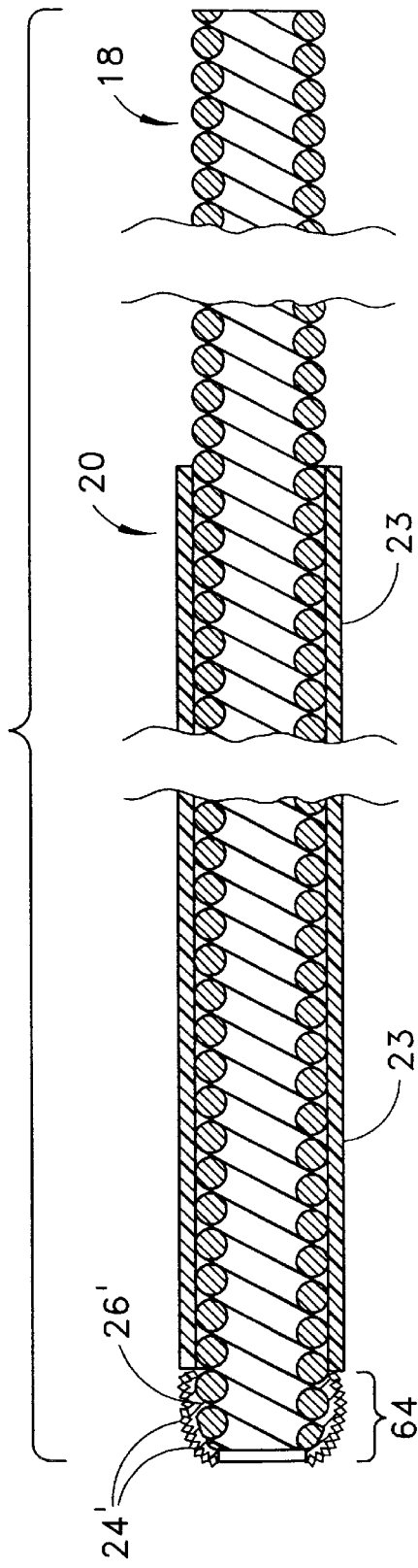
FIGS. 31A and 31B are broken-away, longitudinal cross-sectional views of atherectomy devices of the invention, each having a distal end segment coated with abrasive material to define a distal end abrasive segment.
Figure 31B:
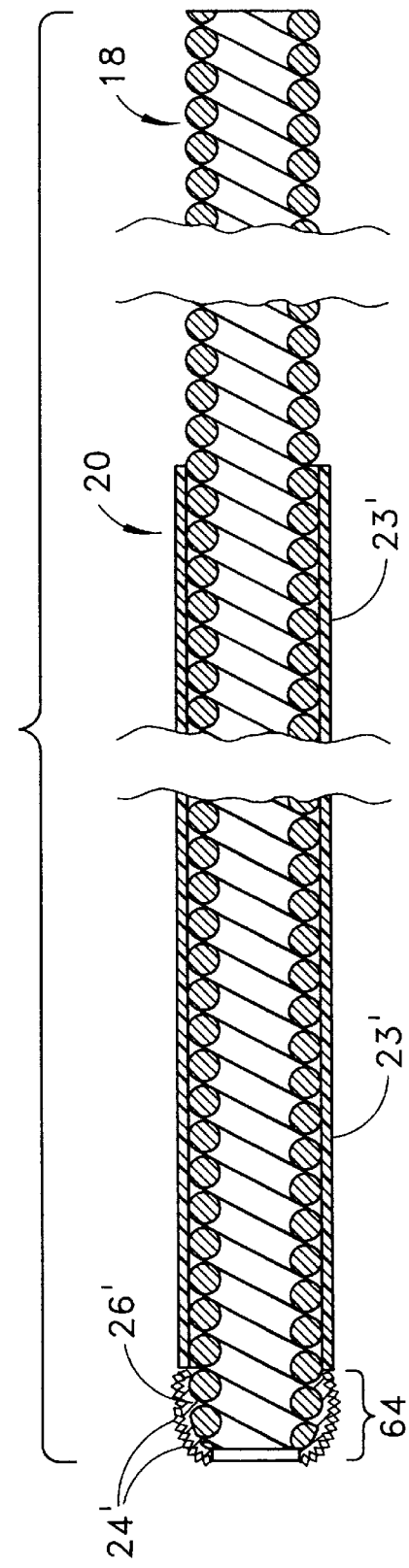

FIGS. 31A and 31B illustrate two embodiments which each utilize an external coating of an abrasive material 24' (secured by a suitable binder 26') on a portion of the distal end segment of the drive shaft 20 to define a single abrasive segment 64 at the distal end of the drive shaft 20. These embodiments thus differ from the atherectomy device depicted in FIG. 11 in that the rotational atherectomy devices of FIGS. 31A and 31B have no enlarged diameter section 28. The abrasive segment 64 preferably has an outer diameter which decreases distally to define a generally convex outer surface—preferably the inner diameter of the distal end segment is generally constant, and, thus, it is the cross-sectional thickness of the wire turns of the abrasive segment 64 which decreases distally to form the generally convex outer surface of the abrasive segment 64 of the drive shaft 20.

The embodiments of both FIGS. 31A and 31B include a thin, flexible, low friction sheath or coating. In FIG. 31A, the sheath or coating 23 is of such a thickness that its outer diameter is approximately equal to the maximum (abrasive coated) outer diameter of the abrasive segment 64. In FIG. 31B, the sheath or coating 23' is thinner—i.e., it is of such a thickness that its outer diameter is less than the maximum (abrasive coated) outer diameter of the abrasive segment 64.

The single abrasive segment 64 of the drive shaft 20 enables the rotating drive shaft of the atherectomy device in both of these embodiments to be advanced across even a very tight stenosis. Such low profile atherectomy devices may be particularly useful in preparing a very tight stenosis for further opening by another atherectomy device, e.g., having an enlarged diameter tissue removal section 28 as described above, or for other medical procedures such as balloon angioplasty.

Figure 32:
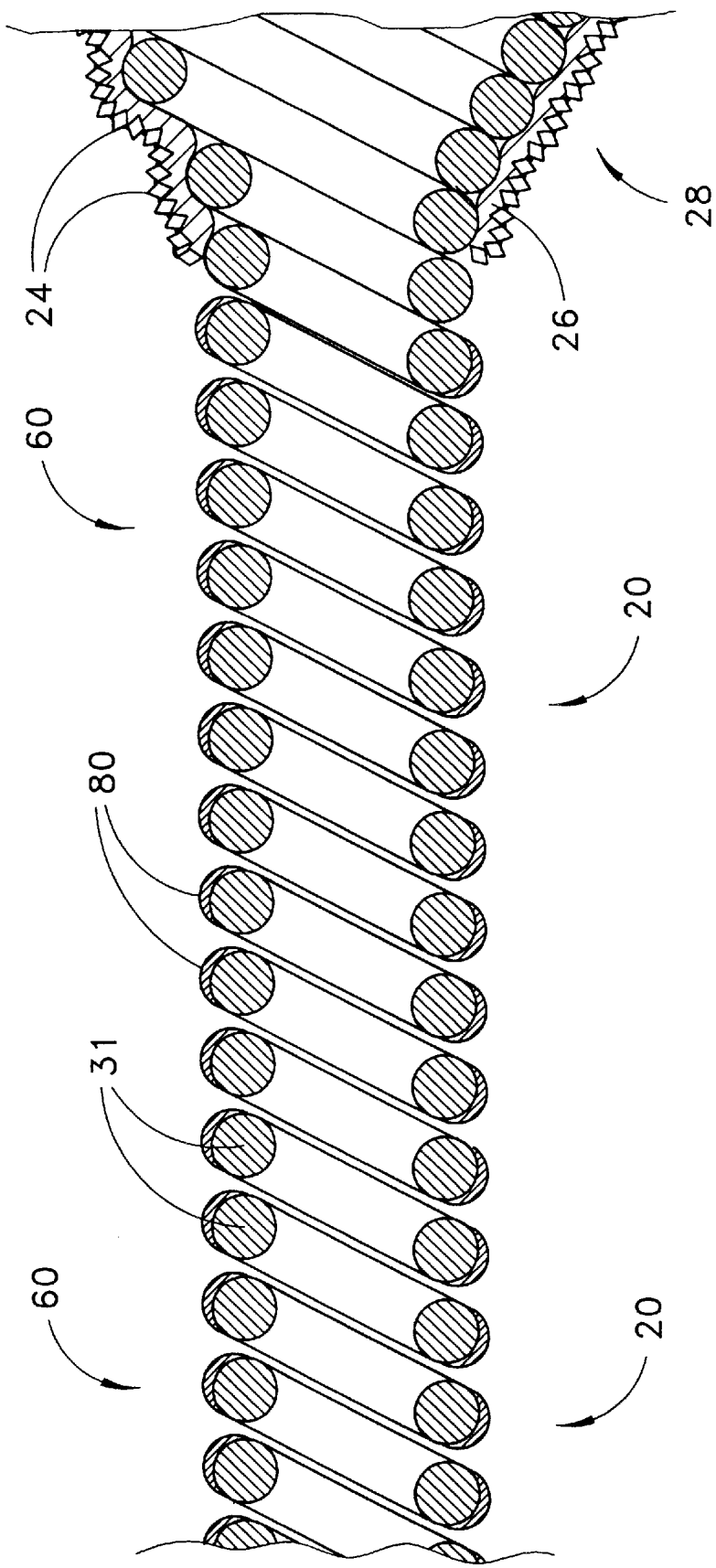
FIG. 32 is a broken-away, longitudinal cross-sectional view of a distal section of a modified atherectomy device of the invention with wire turns of the distal section having a thin external coating of a radio-opaque material.
Figure 33:
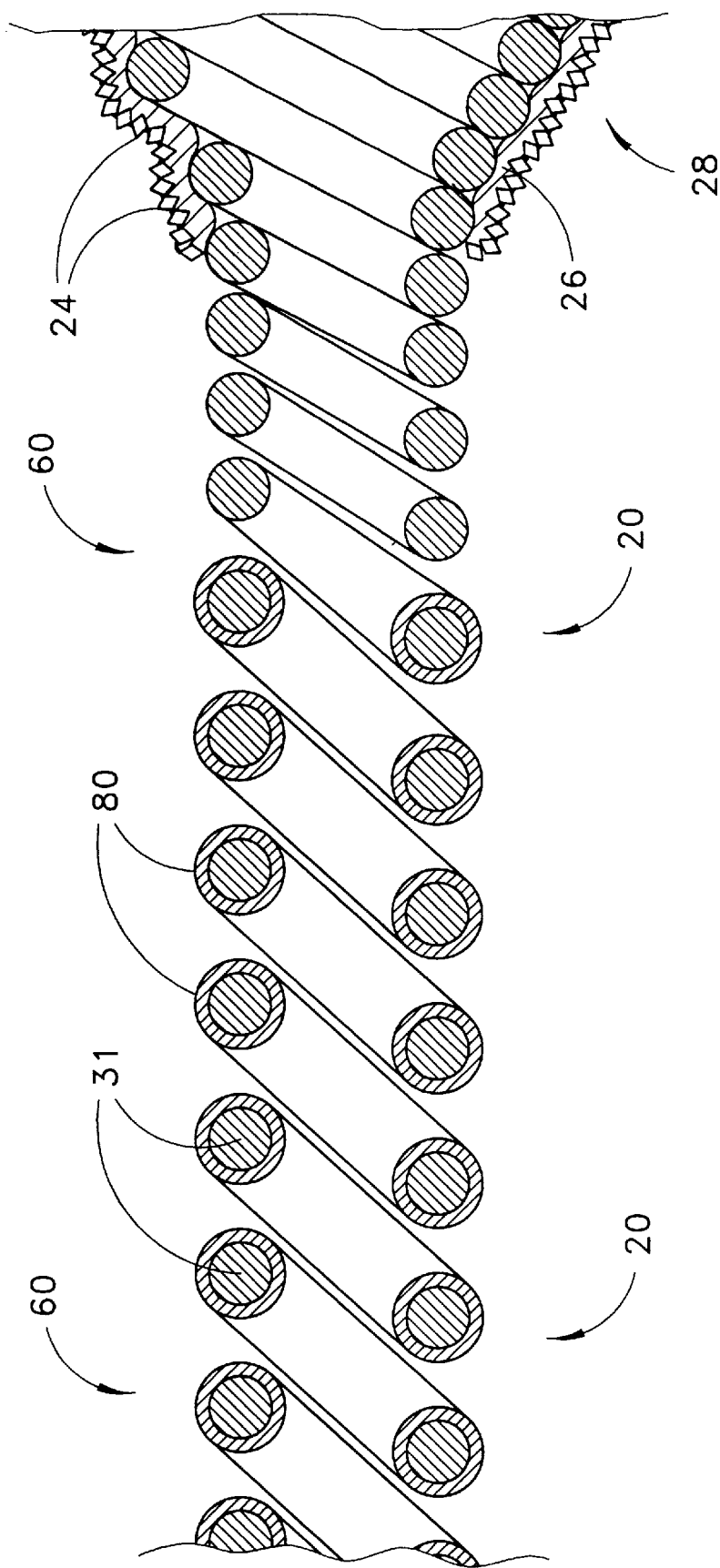
FIG. 33 is a broken-away, longitudinal cross-sectional view of a distal section of a modified embodiment similar to FIG. 32, but with the radio-opaque material coating the entire circumference of wire turns in the distal section of the atherectomy device.

To enhance the visibility of atherectomy devices of the invention during use, it may be desirable to include markers that are substantially more radio-opaque than stainless steel on various portions of the atherectomy device. FIG. 32 illustrates use of a radio-opaque coating 80 deposited on the outer surface of wire turns 31 of a substantial portion of the distal section 60 of the drive shaft 20. Suitable coatings may be obtained by deposition of platinum or other radio-opaque alloys. In FIG. 33, the radio-opaque material 80 is shown as entirely encapsulating the wire turns 31 of a substantial portion of the distal section 60 of the drive shaft 20 (but the radio-opaque material does not fixate adjacent turns 31 of the drive shaft to one another, thus preserving the flexibility of the distal section 60 of the drive shaft).

Figure 34:
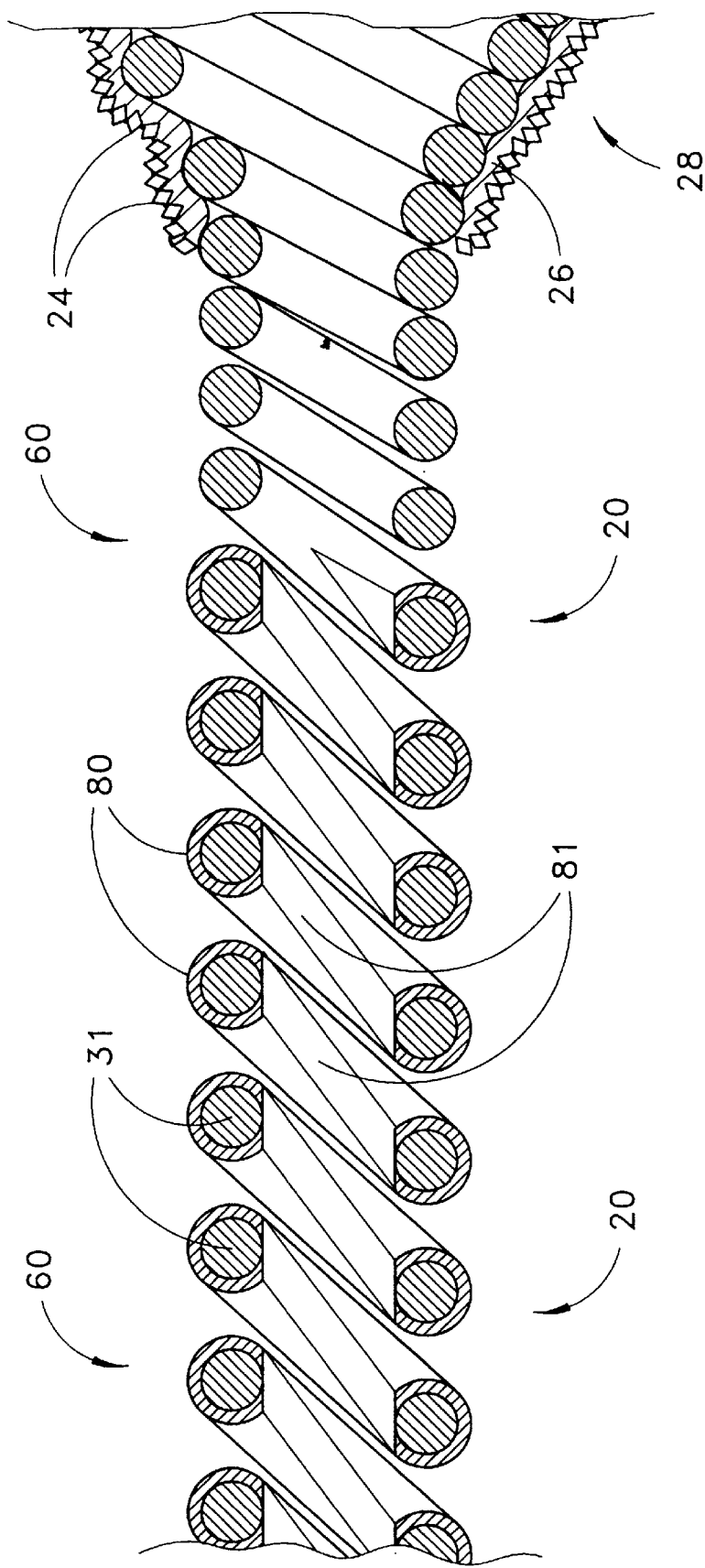
FIG. 34 is a broken-away, longitudinal cross-sectional view of a distal section of another modified embodiment similar to FIG. 33, but with the radio-opaque material coating all but the inner surface of wire turns in the distal section of the atherectomy device.

FIG. 34 illustrates a variation of FIG. 33 in which the radio-opaque material 80 deposited on the wire turns 31 of drive shaft's distal section 60 uniformly covers the wire turns 31 except for the inner surface of the wire turns 31. Such a configuration may be obtained by first coating the wire turns 31 uniformly with the radio-opaque material 80 and then removing that portion of the material which would otherwise reduce the inner diameter of the drive shaft lumen, therefore leaving generally flat inner surfaces 81 on the wire turns 31 as shown in the drawing. Alternately a mandrel or similar device may be placed in the drive shaft lumen before coating the wire turns 31 with radio-opaque material 80 so as to prevent reduction of the inner diameter of this portion of the drive shaft by the radio-opaque material 80. Other suitable manufacturing techniques may also be utilized.

Figure 35:
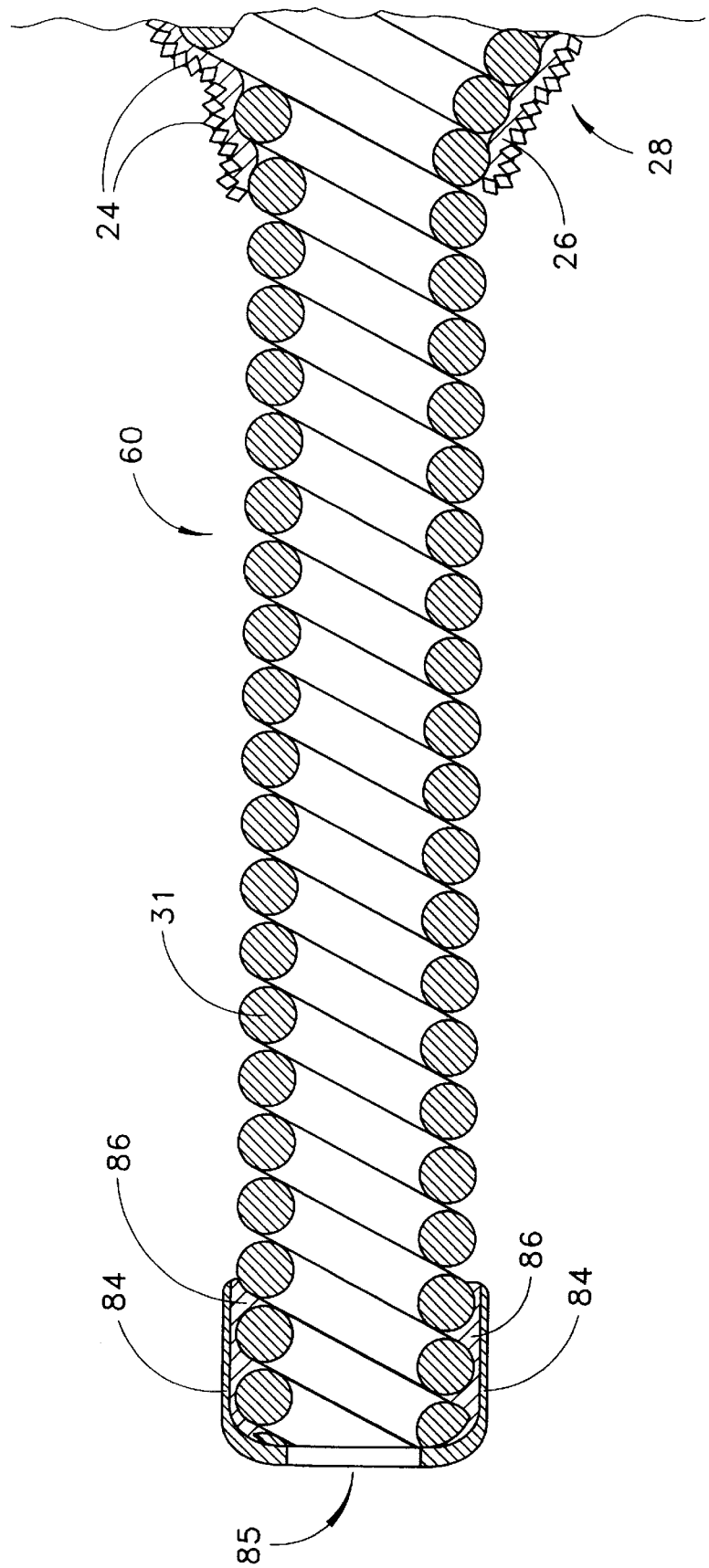
FIG. 35 is a broken-away, longitudinal cross-sectional view of a distal section of a modified atherectomy device of the invention with the distal end encapsulated by a generally cylindrical ring made from a radio-opaque material.

FIG. 35 illustrates use of a marker in the form of a platinum or other suitable radio-opaque collar 84 secured (such as by solder 86 or other suitable material) to the distal end of the distal section 60 of the drive shaft. The collar 84 includes a distal end having an opening 85 with an inner diameter equal to or larger than the inner diameter of the drive shaft lumen. The collar 84 provides good radiological imaging of the distal end of the rotational atherectomy device, and the solder attaching the collar 84 to the wire turns 31 also serves to secure the wire turns 31 of the distal end segment 64 of the drive shaft to one another.

FIGS. 36–41 depict alternative techniques for finishing the distal end segment of the drive shaft. In FIGS. 36 and 37, the very distal ends of the wire turns 31 are first rounded off (as by machining) to the profile depicted in FIG. 36. The distal end segment 64 is then coated with a suitable bonding material 87 to secure the wire turns 31 to one another (FIG. 37). Applicants have found that electro-deposition (i.e., electroplating) of nickel provides desirable results. By masking the inner surfaces of the wire turns 31, nickel is electro-deposited only on the outer surfaces of the wire turns 31 so that the inner diameter of the drive shaft 20 is not affected. The above-described masking may be accomplished by filling the lumen of the drive shaft with a shaft or filament made from tetrafluoroethylene or other suitable materials.

FIGS. 38 and 39 depict an alternative technique in which, rather than rounding off the distal end of the drive shaft 20 (as is depicted in FIG. 36), the distal end of the drive shaft is simply trimmed off "square" and then electroplated as described above.

FIGS. 40 and 41 depict a particularly preferred technique in which the distal end segment 64 is electroplated before being trimmed to its finished length, as shown in FIG. 40. After electroplating is completed, the drive shaft 20 is trimmed to its finished length and the distal end segment 64 may be rounded off (as by machining) to form a generally convex outer surface of the distal end segment of the drive shaft, as depicted in FIG. 41. This technique has the advantage that final machining of the distal end segment 64 to its finished profile is more easily accomplished when the wire turns 31 have been secured to one another by the electro-deposition material.

In any of the embodiments of FIGS. 36–41 the plating metal 87 may optionally include metals that are more radio-opaque than stainless steel. As noted above, nickel, which is somewhat more radio-opaque than stainless steel, may be used as an electro-deposition metal. If desired, an overcoat of platinum (or other highly radio-opaque material) may be deposited over the nickel layer, or may be sandwiched between successive layers of nickel. Applicants have also found that electro-deposited nickel may be used as a binder to secure abrasive material to the distal end segment 64, as described above, e.g., with reference to FIG. 9.

Figure 42:
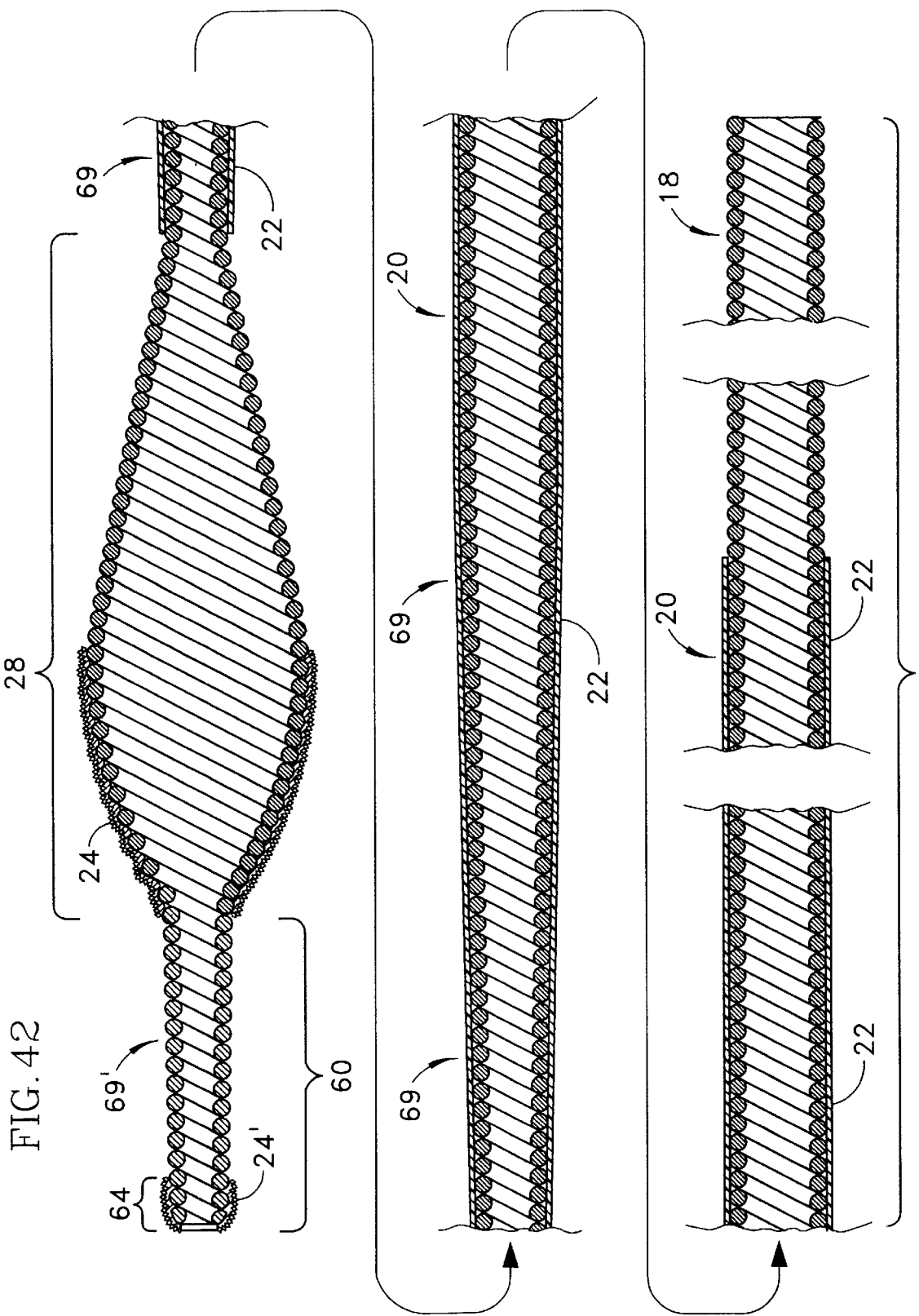
FIG. 42 is a broken-away, longitudinal cross-sectional view of a modified embodiment of the invention having a drive shaft with two distally tapered segments.
Figure 43:
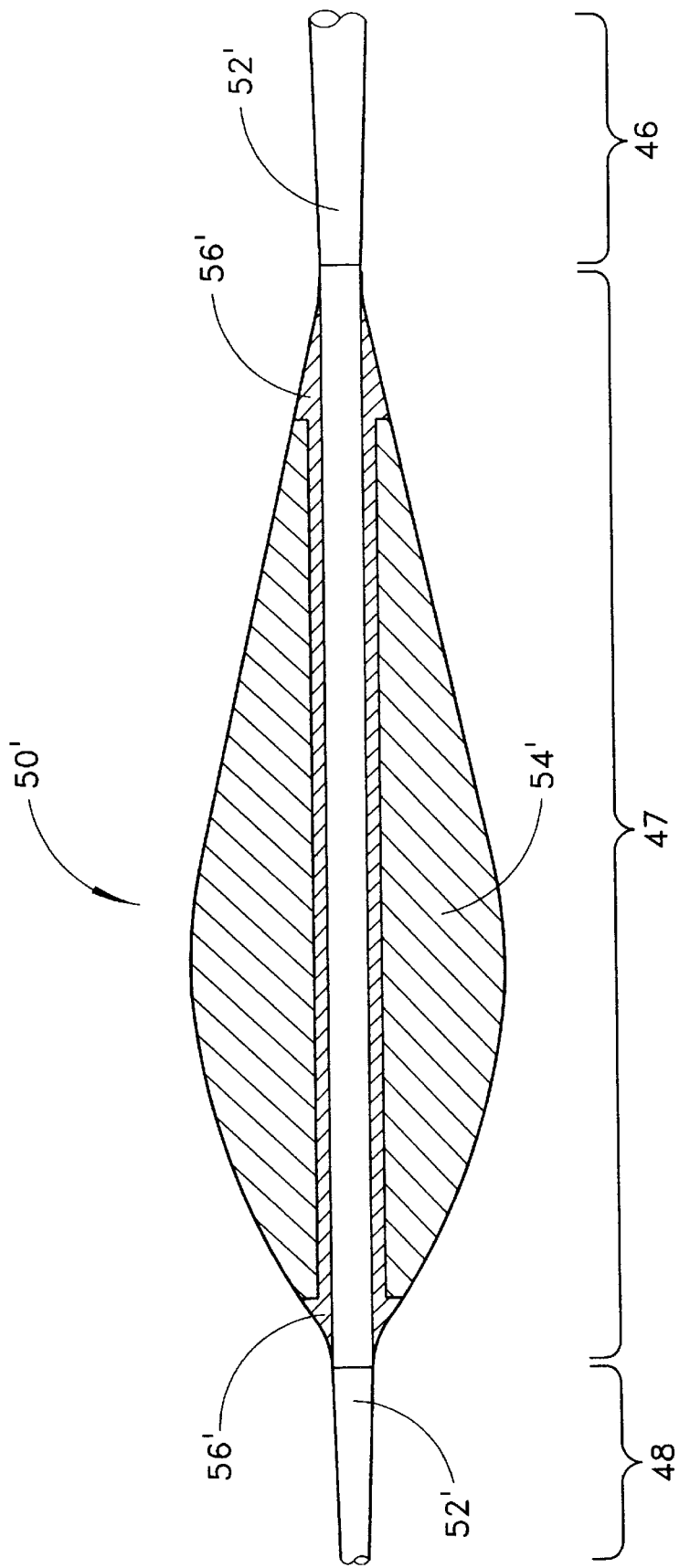
FIG. 43 is a broken-away, longitudinal cross-sectional view of a mandrel used in manufacturing the atherectomy device of FIG. 42.

FIG. 42 depicts a rotational atherectomy device having a drive shaft 20 with generally constant inner and outer diameters along most of its length. It also has two distally tapered segments 69 and 69', one (69) being just proximal to the enlarged diameter section 28, and the other (69') being in the distal section 60 of the drive shaft 20. FIG. 43 is a broken-away, longitudinal cross-sectional view of a mandrel 50' which may be used to manufacture an atherectomy device having a drive shaft 20 with the tapered profile depicted in FIG. 42. The mandrel 50' is similar in most respects to the mandrel 50 depicted in FIG. 8, except that its mandrel shaft 52' is tapered distally along both a proximal section 46 and a distal section 48, the intermediate section 47 having a generally constant diameter. Such mandrel shafts can be manufactured using, e.g., computer controlled centerless grinding systems available from Glebar Company of Franklin Lakes, N.J. The degree of taper is somewhat exaggerated in FIGS. 42–43 for illustrative purposes.

While a preferred embodiment of the present invention has been described, it should be understood that various changes, adaptations and modifications may be made therein without departing from the spirit of the invention and the scope of the appended claims.

What is claimed is:

1. An atherectomy device comprising a flexible, elongated drive shaft having proximal and distal ends, the drive shaft near its distal end, including an enlarged diameter tissue removal section having proximal and distal portions and being comprised of at least one helically wound wire, the proximal portion of the enlarge diameter tissue removal section comprising the entire portion of the enlarged diameter tissue removal section that is proximal to a point of maximum diameter of the enlarged diameter tissue removal section, wire turns of the proximal portion of the tissue removal section having diameters that increase distally at a constant rate thereby forming generally the shape of a cone extending for the entire length or nearly the entire length of the proximal portion of the tissue removal section, at least part of the tissue removal section having an abrasive surface defining an abrasive segment of the drive shaft.

2. The atherectomy device of claim 1 wherein wire turns of the distal portion of the enlarged diameter tissue removal section have diameters that gradually decrease distally thereby forming a generally convex distal portion.

3. The atherectomy device of claim 1 wherein the tissue removal section of the drive shaft is comprised of two or more helically wound wires.

4. The atherectomy device of claim 1 wherein the abrasive surface covers at least the distal portion of the tissue removal section.

5. The atherectomy device of claim 1 wherein the abrasive surface covers at least part of the distal portion of the tissue removal section.

6. The atherectomy device of claim 1 wherein at least some of the wire turns of the abrasive segment of the drive shaft are secured to one another.

7. The atherectomy device of claim 1 wherein the abrasive surface comprises an external coating of abrasive material including a binder for bonding the abrasive material to wire turns of the drive shaft, the binder also securing at least some of the wire turns of the abrasive segment of the drive shaft to one another.

8. The atherectomy device of claim 1 wherein substantially the entire length of the drive shaft is comprised of one or more helically wound wires, such wire(s) being continuous with the wire(s) forming the enlarged diameter tissue removal section of the drive shaft.

9. The atherectomy device of claim 1 wherein wire turns of the distal portion of the enlarged diameter tissue removal section have diameters that gradually decrease distally thereby forming a generally convex distal portion having, in longitudinal cross-section, a first radius of curvature.

10. The atherectomy device of claim 9 wherein the tissue removal section includes an intermediate transitional portion having wire turns with diameters that gradually change so that such transitional portion forms a generally convex shape having, in longitudinal cross-section, a second radius of curvature, thereby providing a smooth transition from the generally conical proximal portion of the tissue removal section to the generally convex distal portion of the tissue removal section.

11. The atherectomy device of claim 10 wherein the first radius of curvature of the distal portion of the tissue removal section is larger than the second radius of curvature of the intermediate transitional portion of the tissue removal section.

12. The atherectomy device of claim 10 wherein the first radius of curvature of the distal portion of the tissue removal section is smaller than the second radius of curvature of the intermediate transitional portion of the tissue removal section.

13. The atherectomy device of claim 1 wherein the enlarged diameter tissue removal section includes an intermediate portion having wire turns with generally constant diameters thereby giving the intermediate portion a generally cylindrical shape.

14. The atherectomy device of claim 1 wherein that section of the elongated drive shaft which is proximal to the enlarged diameter tissue removal section has generally constant cross-sectional inner and outer diameters along substantially its entire length except for a reduced diameter segment located near the enlarged diameter tissue removal section, such reduced diameter segment having both inner and outer diameters reduced relative to immediately adjacent portions of the drive shaft.

15. The atherectomy device of claim 14 further comprising a length of low-friction tubing disposed over the reduced diameter segment and at least a substantial portion of the proximal section of the drive shaft, the portion of tubing disposed over the reduced diameter segment of the drive shaft having an inner diameter less than the inner diameter of adjacent portions of the tubing, thereby securing the tubing against longitudinal movement with respect to the drive shaft.

16. The atherectomy device of claim 14 including two or more reduced diameter segments located close to one another, the most distal one of such segments being located near the enlarged diameter tissue removal section.

17. The atherectomy device of claim 16 further comprising a length of low-friction tubing disposed over the reduced diameter segments and at least a substantial portion of the proximal section of the drive shaft, the portions of tubing disposed over the reduced diameter segments of the drive shaft having an inner diameter less than the inner diameter of adjacent portions of the tubing, thereby securing the tubing against longitudinal movement with respect to the drive shaft.

18. The atherectomy device of claim 14 wherein the reduced diameter segment is located within about one inch from the enlarged diameter tissue removal section.

19. The atherectomy device of claim 14 wherein the reduced diameter segment is located within about one quarter inch from the enlarged diameter tissue removal section.

20. The atherectomy device of claim 1 wherein that section of the elongated drive shaft which is distal to the enlarged diameter tissue removal section has generally constant cross-sectional inner and outer diameters along substantially its entire length except for a reduced inner and outer diameter segment located near the enlarged diameter tissue removal section.

21. The atherectomy device of claim 20 further comprising a length of low-friction tubing disposed over the reduced diameter segment and at least a substantial portion of the distal section of the drive shaft, the portion of tubing disposed over the reduced diameter segment of the drive shaft having an inner diameter less than the inner diameter of adjacent portions of the tubing, thereby securing the tubing against longitudinal movement with respect to the drive shaft.

22. The atherectomy device of claim 20 including two or more reduced diameter segments located close to one another, the most proximal one of such segments being located near the enlarged diameter tissue removal section.

23. The atherectomy device of claim 22 further comprising a length of low-friction tubing disposed over the reduced diameter segments and at least a substantial portion of the distal section of the drive shaft, the portions of tubing disposed over the reduced diameter segments of the drive shaft having an inner diameter less than the inner diameter of adjacent portions of the tubing, thereby securing the tubing against longitudinal movement with respect to the drive shaft.

24. The atherectomy device of claim 20 wherein the reduced diameter segment is located within about one inch from the enlarged diameter tissue removal section.

25. The atherectomy device of claim 20 wherein the reduced diameter segment is located within about one quarter inch from the enlarged diameter tissue removal section.

26. The atherectomy device of claim 1 wherein that section of the elongated drive shaft which is proximal to the enlarged diameter tissue removal section has generally constant cross-sectional inner and outer diameters along substantially its entire length except for a first reduced inner and outer diameter segment located proximally to the enlarged diameter tissue removal section; and wherein that section of the elongated drive shaft which is distal to the enlarged diameter tissue removal section has generally constant cross-sectional inner and outer diameters along substantially its entire length except for a second reduced inner and outer diameter segment located distally to the enlarged diameter tissue removal section.

27. The atherectomy device of claim 1 wherein that section of the elongated drive shaft which is proximal to the enlarged diameter tissue removal section has generally constant cross-sectional inner and outer diameters along substantially its entire length; and wherein that section of the elongated drive shaft which is distal to the enlarged diameter tissue removal section also has generally constant cross-sectional inner and outer diameters along substantially its entire length, the inner and outer diameters of such distal section of the drive shaft being smaller than the corresponding inner and outer diameters of the proximal section of the drive shaft.

28. The atherectomy device of claim 1 wherein that section of the elongated drive shaft which is proximal to the enlarged diameter tissue removal section has generally constant cross-sectional inner and outer diameters along substantially its entire length except for a reduced inner and outer diameter segment located proximal to the enlarged diameter tissue removal section; the section of the elongated drive shaft which is distal to the enlarged diameter tissue removal section having generally constant cross-sectional inner and outer diameters along substantially its entire length, the inner and outer diameters of such distal section of the drive shaft being smaller than the inner and outer diameters along substantially the entire length of the proximal section of the drive shaft.

29. The atherectomy device of claim 1 wherein the drive shaft includes a distal end segment having a layer of electro-deposition material securing adjacent wire turns of the drive shaft to one another.

30. The atherectomy device of claim 29 wherein the electro-deposition material is more radio-opaque than stainless steel.

31. The atherectomy device of claim 29 wherein the distal end segment has a distal most wire turn with an outer diameter which is less than an outer diameter of a wire turn immediately proximal to such distal wire turn.

32. The atherectomy device of claim 31 wherein the inner diameter of the distal end segment is generally constant, the cross-sectional thickness of the wire turns of the distal end segment, in longitudinal cross-section, decreasing distally to form the generally convex outer surface of the distal end segment of the drive shaft.

33. The atherectomy device of claim 31 wherein at least a portion of the distal end segment is provided with an external coating of an abrasive material to define a second abrasive segment at the distal end of the drive shaft.

34. The atherectomy device of claim 1 wherein the elongated drive shaft includes a distal end segment having an outer diameter which, in longitudinal crosssection, decreases distally to define a generally convex outer surface.

35. The atherectomy device of claim 31 wherein the inner diameter of the distal end segment is generally constant, the cross-sectional thickness of the wire turns of the distal end segment, in longitudinal cross-section, decreasing distally to form the generally convex outer surface of the distal end segment of the drive shaft.

36. The atherectomy device of claim 31 wherein at least a portion of the distal end segment is provided with an external coating of an abrasive material to define a second abrasive segment at the distal end of the drive shaft.

37. An atherectomy device comprising a flexible, elongated drive shaft, the drive shaft including an enlarged diameter tissue removal section having proximal and distal portions and being comprised of at least one helically wound wire, wire turns of the proximal portion of the tissue removal section having diameters that increase distally at a generally constant rate thereby forming generally the shape of a cone, wire turns of the distal portion of the enlarged diameter tissue removal section have diameters that gradually decrease distally thereby forming a generally convex distal portion, at least part of the tissue removal section having an abrasive surface defining an abrasive segment of the drive shaft;

that section of the elongated drive shaft which is proximal to the enlarged diameter tissue removal section having generally constant cross-sectional inner and outer diameters along substantially its entire length except for a reduced diameter segment located within about one inch from the enlarged diameter tissue removal section, such reduced diameter segment having both inner and outer diameters reduced relative to immediately adjacent portions of the drive shaft;

that section of the elongated drive shaft which is distal to the enlarged diameter tissue removal section having generally constant cross-sectional inner and outer diameters along substantially its entire length, the inner and outer diameters of such distal section of the drive shaft being smaller than the corresponding inner and outer diameters of the drive shaft along substantially the entire length of the drive shaft proximal to the enlarged diameter tissue removal section.

38. An atherectomy device comprising a guide wire having a generally constant cross-sectional diameter along substantially its entire length; and a flexible, elongated drive shaft comprised of one or more helically wound wires defining a central lumen in which the guide wire is disposed, the drive shaft including an enlarged diameter tissue removal section; substantially the entire length of the drive shaft having a generally constant cross-sectional inner diameter except for the enlarged diameter tissue removal section and a reduced diameter segment located near the tissue removal section to function as a bearing to facilitate smooth rotation of the drive shaft about the guide wire, said reduced diameter segment being reduced relative to said generally constant cross-sectional inner diameter.

39. The atherectomy device of claim 38 wherein the reduced diameter segment has both inner and outer diameters reduced relative to immediately adjacent portions of the drive shaft.

40. The atherectomy device of claim 39 further comprising a length of low-friction tubing disposed over the reduced diameter segment and at least a substantial portion of the drive shaft, the portion of tubing disposed over the reduced diameter segment of the drive shaft having an inner diameter less than the inner diameter of adjacent portions of the tubing, thereby securing the tubing against longitudinal movement with respect to the drive shaft.

41. The atherectomy device of claim 38 including two or more reduced diameter segments, at least one being located distally of the enlarged diameter tissue removal section, and at least one being located proximally of the enlarged diameter tissue removal section.

42. The atherectomy device of claim 38 including two or more reduced diameter segments located proximally of the enlarged diameter tissue removal section, the segments being located close to one another and the most distal one of such segments being located near the enlarged diameter tissue removal section.

43. The atherectomy device of claim 38 including two or more reduced diameter segments located distally of the enlarged diameter tissue removal section, the segments being located close to one another and the most proximal one of such segments being located near the enlarged diameter tissue removal section.

44. The atherectomy device of claim 38 wherein the reduced diameter segment is located within about one inch from the enlarged diameter tissue removal section.

45. The atherectomy device of claim 38 wherein the reduced diameter segment is located within about one quarter inch from the enlarged diameter tissue removal section.

46. An atherectomy device comprising a flexible, elongated drive shaft, the drive shaft including an enlarged diameter tissue removal section having a generally conical proximal portion and a generally convex distal portion, the drive shaft being comprised of at least one helically wound wire, at least part of the distal portion of the enlarged diameter tissue removal section including an external coating of an abrasive material secured to the wire turns of the drive shaft to define an abrasive segment of the drive shaft, at least a substantial portion of the wire turns of the abrasive segment, including the more proximal wire turns of the abrasive segment, being secured to one another; the maximum outer diameter and length of the abrasive segment being selected so that, at operational rotational speeds and under load, at least some of the wire turns of the proximal portion of the enlarged diameter tissue removal section unwind from their at-rest diameter to an effective outer diameter which is at least as large as the maximum outer diameter of the abrasive segment.

47. The atherectomy device of claim 46, wherein the maximum outer diameter and length of the abrasive segment being selected so that, at operational rotational speeds and under load, at least some of the wire turns of the proximal portion of the enlarged diameter tissue removal section unwind from their at-rest diameter to an effective outer diameter which is larger than the maximum outer diameter of the abrasive segment.

\* \* \* \* \*